US010895547B2

(12) United States Patent
Webber

(10) Patent No.: US 10,895,547 B2
(45) Date of Patent: Jan. 19, 2021

(54) POTTING MOISTURE DETECTION SYSTEM AND METHOD

(71) Applicant: Mueller International, LLC, Atlanta, GA (US)

(72) Inventor: Gary Lee Webber, Sharon, MA (US)

(73) Assignee: Mueller International, LLC, Atlanta, GA (US)

( * ) Notice: Subject to any disclaimer, the term of this patent is extended or adjusted under 35 U.S.C. 154(b) by 283 days.

(21) Appl. No.: 16/179,207

(22) Filed: Nov. 2, 2018

(65) Prior Publication Data

US 2020/0141889 A1 May 7, 2020

(51) Int. Cl.
*G01N 27/04* (2006.01)
*G01N 33/24* (2006.01)

(52) U.S. Cl.
CPC ......... *G01N 27/048* (2013.01); *G01N 33/246* (2013.01); *G01N 2033/245* (2013.01)

(58) Field of Classification Search
CPC .............. G01N 27/048; G01N 33/246; G01N 2033/245
See application file for complete search history.

(56) References Cited

U.S. PATENT DOCUMENTS

| 2003/0000303 A1* | 1/2003 | Livingston | ............ | G01F 23/266 73/304 C |
| 2017/0258643 A1* | 9/2017 | Xu | ........................ | B29C 66/45 |
| 2020/0181824 A1* | 6/2020 | Vitali | ..................... | D06F 34/04 |

OTHER PUBLICATIONS

Wikipedia; Article entitled: "Three-state logic", located at <https://en.wikipedia.org/wiki/Three-state_logic>, accessed on Oct. 19, 2018, 3 pgs.
Article entitled: "Digital Buffer and Tri-state Buffer Tutorial", located at <https://www.electronics-tutorials.ws/logic/logic_9.html>, accessed on Oct. 19, 2018, 14 pgs.
Sparkfun; Article entitled: "Analog to Digital Conversion", located at <https://learn.sparkfun.com/tutorials/analog-to-digital-conversion>, accessed on Sep. 10, 2018, 4 pgs.

* cited by examiner

*Primary Examiner* — Alvaro E Fortich
*Assistant Examiner* — Zannatul Ferdous
(74) *Attorney, Agent, or Firm* — Taylor English Duma LLP

(57) ABSTRACT

A node includes a circuit board assembly having a circuit board and a processor mounted to the circuit board, the processor comprising a pin and an analog-to-digital converter (ADC) in electrical communication with the pin, the circuit board defining a test point formed therein, the test point electrically communicating with the pin via a trace covered with an insulator; and a non-transitory memory resource, the non-transitory memory resource having computer-executable instructions stored thereon that, when executed by the processor, cause the processor to apply electrical charge to the test point after the circuit board assembly has been encased in potting compound, and command the ADC to read a test point voltage at the test point, the test point voltage indicating voltage of an equivalent RC circuit comprising the insulator as an equivalent capacitor and the potting compound as an equivalent resistor.

15 Claims, 14 Drawing Sheets

POTTING MOISTURE DETECTION SYSTEM AND METHOD

TECHNICAL FIELD

This disclosure relates to nodes within a wireless network. More specifically, this disclosure relates to detection of moisture in potting compound contained within a node of a wireless network.

BACKGROUND

A utility provider, such as a gas, electricity, or water provider, may have a large number of control, measuring, and sensing devices installed in the field in order to control transmission and distribution of the product, measure, and record product usage, and detect problems. Such devices may include water, gas, or electrical meters, remotely controlled valves, flow nodes, leak detection devices, and the like. Utility meters may include wireless communication capability to send and receive wireless communications with a remote communication device, enabling remote reading of meters.

Advanced Metering Infrastructure (AMI), Automatic Meter Reading (AMR), and Advanced Metering Management (AMM) are systems that measure, collect, and analyze utility data using advanced metering devices such as water meters, gas meters, and electricity meters. A typical AMI network may include thousands of nodes. A "node" as used herein may refer to either a composite device in a network capable of performing a specific function or a communication module connected to such a device and configured to provide communications for the device. The AMI network also includes a device known as a repeater, which receives a signal from a central network device, such as a hub, and that regenerates the signal for distribution to other network devices. Nodes and some repeaters can be powered by direct current, supplied by batteries (DC powered), while other repeaters are alternating-current (AC) powered.

AMI networks are typically characterized by two-way communication between a node and another network device or devices. In a typical, fixed AMI configuration, an AMI system may comprise a central host capable of connecting via wired and/or wireless networking infrastructures to a number of communication nodes, each node providing network communications for one or more connected metering devices, control devices, sensor devices, or the like. The AMI system may further include data collection hubs, repeaters, gateways, and the like.

Each node can include a potting compound to protect a printed circuit board assembly placed within the housing of the node. The potting compound is typically a semi-solid substance that is typically comprised of two parts, one polyol, and the other isocyanate. Although the potting compound generally performs well in its function of protecting the circuit board assembly against outdoor elements, occasionally small cracks may develop in the potting compound over time. The introduction of moisture into the node may interfere with the functioning of one or more components on the circuit board, including but not limited to a crystal oscillator functioning as the node's internal clock, impairing the ability of the node to perform tasks such as taking meter readings and reporting them to another network element, such as a host. Although one way to address this moisture problem would be to retrofit such nodes with separate moisture detection devices (such as sensors and associated hardware), the cost of doing so would be prohibitively high.

SUMMARY

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

In an aspect of the present disclosure, a node can comprise a circuit board assembly comprising a circuit board and a processor mounted to the circuit board, the processor comprising a pin and an analog-to-digital converter (ADC) in electrical communication with the pin, the circuit board defining a test point formed therein, the test point electrically communicating with the pin via a trace covered with an insulator; and a non-transitory memory resource, the non-transitory memory resource having computer-executable instructions stored thereon that, when executed by the processor, cause the processor to apply electrical charge to the test point after the circuit board assembly has been encased in potting compound, and command the ADC to read a test point voltage at the test point, the test point voltage indicating voltage of an equivalent resistor-capacitor (RC) circuit comprising the insulator as an equivalent capacitor and the potting compound as an equivalent resistor.

In another aspect of the present disclosure, a potting moisture detection system can comprise a host, the host configured to communicate a command to a plurality of nodes and to receive data from at least one node in the plurality of nodes responsive to the command; and a node of the type described above, the node configured to send point value data to the host responsive to receiving a command from the host to transmit the point value data.

In yet another aspect of the present disclosure, a method can comprise the steps of applying electrical charge to a test point in a circuit board assembly after the circuit board assembly has been encased in potting compound, the circuit board assembly comprising a circuit board and a processor mounted to the circuit board, the processor comprising a pin and an analog-to-digital converter (ADC) in electrical communication with the pin, the circuit board defining a test point formed therein, the test point electrically communicating with the pin via a trace covered with an insulator, and after lapse of a predetermined delay period, commanding the ADC to read a test point voltage at the test point, the test point voltage indicating voltage of an equivalent resistor-capacitor (RC) circuit comprising the insulator as an equivalent capacitor and the potting compound as an equivalent resistor.

Various implementations described in the present disclosure can comprise additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims. The features and advantages of such implementations can be realized and obtained by means of the systems, methods, features particularly pointed out in the appended claims. These and other features will become more fully apparent from the following description and appended claims, or can be learned by the practice of such exemplary implementations as set forth hereinafter.

BRIEF DESCRIPTION OF THE DRAWINGS

The features and components of the following figures are illustrated to emphasize the general principles of the present disclosure. Corresponding features and components throughout the figures can be designated by matching reference characters for the sake of consistency and clarity.

FIG. 12 shows a test point going through insulating coating.

DETAILED DESCRIPTION

Figure 1:
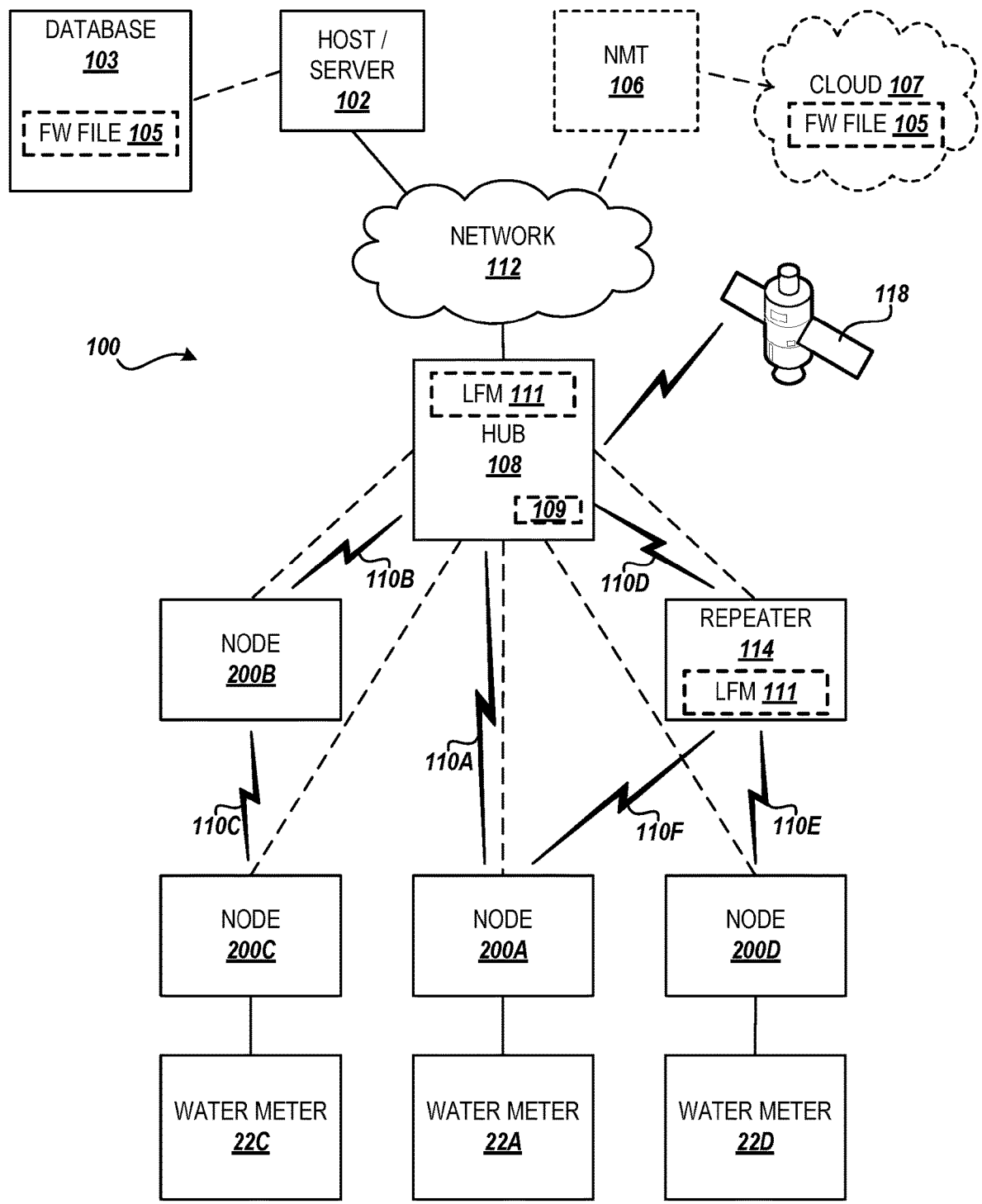
FIG. 1 is a block diagram showing one example of a network topology employing nodes constructed according to certain embodiments described herein.

The present disclosure can be understood more readily by reference to the following detailed description, examples, drawings, and claims, and their previous and following description. However, before the present devices, systems, and/or methods are disclosed and described, it is to be understood that this disclosure is not limited to the specific devices, systems, and/or methods disclosed unless otherwise specified, as such can, of course, vary. It is also to be understood that the terminology used herein is for the purpose of describing particular aspects only and is not intended to be limiting.

The following description is provided as an enabling teaching of the present devices, systems, and/or methods in their best, currently known aspect. To this end, those skilled in the relevant art will recognize and appreciate that many changes can be made to the various aspects described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

As used throughout, the singular forms "a," "an" and "the" include plural referents unless the context clearly dictates otherwise. Thus, for example, reference to a quantity of one of a particular element can comprise two or more such elements unless the context indicates otherwise.

Ranges can be expressed herein as from "about" one particular value, and/or to "about" another particular value. When such a range is expressed, another aspect comprises from the one particular value and/or to the other particular value. Similarly, when values are expressed as approximations, by use of the antecedent "about" or substantially," it will be understood that the particular value forms another aspect. It will be further understood that the endpoints of each of the ranges are significant both in relation to the other endpoint, and independently of the other endpoint.

For purposes of the present disclosure, a material property or dimension measuring about X or substantially X on a particular measurement scale measures within a range between X plus an industry-standard upper tolerance for the specified measurement and X minus an industry-standard lower tolerance for the specified measurement. Because tolerances can vary between different materials, processes and between different models, the tolerance for a particular measurement of a particular component can fall within a range of tolerances.

As used herein, the terms "optional" or "optionally" mean that the subsequently described event or circumstance may or may not occur, and that the description comprises instances where said event or circumstance occurs and instances where it does not.

The word "or" as used herein means any one member of a particular list and also comprises any combination of members of that list.

To simplify the description of various elements disclosed herein, the conventions of "top," "bottom," "side," "upper," "lower," "horizontal," and/or "vertical" may be referenced. Unless stated otherwise, "top" describes that side of the system or component that is facing upward and "bottom" is that side of the system or component that is opposite or distal the top of the system or component and is facing downward. Unless stated otherwise, "side" describes that an end or direction of the system or component facing in horizontal direction. "Horizontal" or "horizontal orientation" describes that which is in a plane aligned with the horizon. "Vertical" or "vertical orientation" describes that which is in a plane that is angled at 90 degrees to the horizontal.

Regarding the term "cloud" as used herein, as explained with regard to cloud computing generally in U.S. Patent Application Publication No. 2014/0379910 to Saxena et al., the cloud disclosed herein can include "a collection of hardware and software that forms a shared pool of configurable computing resources (e.g., networks, servers, storage, applications, services, etc.), which can be suitably provisioned to provide on-demand self-service, network access, resource pooling, elasticity and measured service, among other features." The cloud disclosed herein can be deployed as a private cloud (e.g., infrastructure operated by a single enterprise/organization), a community cloud (e.g., infrastructure shared by several organizations to support a specific community that has shared concerns), a public cloud (e.g., infrastructure made available to the general public, such as the Internet), or a suitable combination of two or more disparate types of clouds. In this description, "cloud computing" is defined as a model for enabling on-demand network access to a shared pool of configurable computing resources (e.g., networks, servers, storage, applications, and services). As stated in U.S. Patent Application Publication No. 2014/0075431 to Kumar et al: "Generally, a cloud computing model enables some of those responsibilities which previously may have been provided by an organization's own information technology department, to instead be delivered as service layers within a cloud environment, for use by consumers (either within or external to the organization, according to the cloud's public/private nature)." As further explained in the aforementioned Kumar et al. patent application, a cloud computing model can take the form of various service models such as, for example, Software as a Service ("SaaS"), "in which consumers use software applications that are running upon a cloud infrastructure, while a SaaS provider manages or controls the underlying cloud infrastructure and applications," and Platform as a Service ("PaaS"), "in which consumers can use software programming languages and development tools supported by a PaaS provider to develop, deploy, and otherwise control their own applications, while the PaaS provider manages or controls other aspects of the cloud environment (i.e., everything below the run-time execution environment)." The definition of "cloud computing" is not limited to any of the other numerous advantages that can be obtained from such models when properly deployed.

Disclosed is a potting moisture detection system that provides for monitoring of moisture in networked nodes without the need to retrofit such nodes with separate detection sensors or devices, or to change any of the internal or external structure of the nodes. Instead, the legacy nodes can be endowed with potting moisture detection capability through the implementation of software instructions that can be stored into an existing memory resource of the node, such as through a broadcast remote firmware update, certain techniques for accomplishing such updates discussed in co-pending U.S. patent application Ser. No. 15/677,138, filed Aug. 15, 2017, the disclosure of which is hereby incorporated by reference herein in its entirety. The system of the present disclosure recognizes that an equivalent resistor-capacitor (RC) circuit exists in the node, with insulator material covering circuit board traces acting as an equivalent capacitor, and the potting compound acting as an equivalent resistor. One can apply electrical charge to that equivalent RC circuit, via a switch in an existing node microprocessor connected to a voltage source, then measuring the resulting voltage at a test point within the circuit board. Repeated cycles of applying the charge to the equivalent RC circuit, and measuring the responsive voltage at that circuit, in a closed loop servo arrangement, allows a user to observe the change in measured voltage over time, which provides an indication of conductance of the combination of the potting compound and the insulator, from which relative moisture content in the potting compound can be ascertained. The user can thus pinpoint which nodes in a network may have a potting moisture content greater than a predetermined threshold for indicating an unacceptable moisture condition. These and other benefits are attendant to the potting moisture detection system and method disclosed herein.

FIG. 1 is a block diagram showing one example of a network topology of an illustrative fixed AMI system (or network) 100, such as that implemented by a utility provider. The present disclosure refers to several devices in an AMI system as either transmitting or receiving broadcast or direct messages, but the methods described in the present disclosure are not to be strictly limited to fixed AMI systems, as such methods can also be used in networks that include, among others, attributes of both AMI and AMR systems, such as those disclosed in co-pending U.S. patent application Ser. No. 15/161,448, filed May 23, 2016, which is hereby incorporated by reference in its entirety.

The AMI system 100 may include utility provider systems, such as host 102. The host 102 may represent a combination of application servers, database servers, communication servers, web servers, and the like that comprise the systems of the utility provider used to collect data from, control, and manage the various nodes 200A-200D (referred to herein generally as nodes 200) in the AMI system 100. For example, as shown in FIG. 1, nodes 200C, 200A, 200D may be respectively connected to water meters 22C, 22A, 22D and provide AMI network communications for the devices. For ease of reference, types of nodes other than hubs 108 (described below) will hereinafter be assigned the general reference numeral 200, unless stated otherwise, with the understanding that nodes 200 may have a construction according to the description of FIG. 2, to be described herein. The host 102 is shown being operatively connected to a database 103 that stores a firmware file 105, which is the file to be sent to other devices in system 100 when firmware updates of other system devices are conducted in the manner described herein.

According to various embodiments, the host 102 may communicate with downstream devices, including the nodes 200 through one or more collection hubs 108. As used herein, "downstream device" includes any device within the system 100, other than the host 102, that is configured to receive any communication originating from the host 102, including from any server comprising the host 102, in whole or in part. Stationary, or fixed, collection hubs 108 may comprise specialized network nodes installed in the field that act as a "parent node" for a set of assigned child nodes 200A-200D that communicate with the hub 108 through various communication links 110A-110E (referred to herein generally as communication links 110). The communication links 110 may include wireless communication links, such as RF communication links, among others. Owing to a stationary transceiver 109 housed in each hub 108, the communication across the communication links 110 is two-way. The collection hubs 108 may periodically collect usage data, node data, and other data from the child nodes 200 and forward data to the host 102 over a network 112. The collection hubs 108 may also forward messages received from the host 102 over the network 112 to the target child node(s) 200. The network 112 may comprise various networking technologies that connect the collection hubs 108 in the field to the host 102, including (among others) cellular data networks, W-Fi or WMAX networks, satellite communication networks, metropolitan-area networks ("MANs"), wide-area networks ("WANs"), the Internet, and the like. In a downstream progression in which a node 200 is the ultimate recipient of a message, the message originates from an upstream source such as the host 102. The host 102 sends the originated message to a transmitting device, such as the hub 108 (FIG. 1) or, in some networks, to a collector. The hub 108 (or collector) then disseminates (broadcasts) the message to certain nodes 200 and, optionally, one or more repeaters 114 (FIG. 1), and from a repeater 114, the broadcast message is further disseminated to certain other nodes 200. A downstream device is "targeted" with filtering information present in one or more message fields within a broadcast message, as exemplified in co-pending U.S. patent application Ser. No. 15/621,619, filed Jun. 13, 2017, the disclosure of which is hereby specifically incorporated by reference herein in its entirety. In one implementation, when a targeted downstream device sends a response, the response is transmitted in an upstream progression, i.e., in the order of system devices opposite that recited for the aforementioned downstream direction.

As an alternative to the combination of the host 102 and database 103, as shown in FIG. 1, the firmware file 105 may be stored in a cloud 107, and a network management tool (NMT) 106 may be communicatively connected to the cloud 107 in order to access and retrieve a copy of the firmware file 105. The NMT 106 may be a computer application that is configured to communicate with clouds such as the cloud 107. The NMT 106 may be operatively connected to the network 112 in the same manner discussed above with regard to the host 102. As used herein, "upstream source" is intended to refer to either the host 102 or the NMT 106, whichever may be preferred to be used in a given system.

The collection hub 108 may communicate with its child nodes 200A-200D either directly or through one or more intermediary devices. For example, the AMI system 100 may include repeaters 114 that facilitate communication between the collection hub 108 and remote nodes, such as node 200D. According to further embodiments, some nodes may be configured to act as repeaters, referred to herein as "buddy nodes," such as node 200B shown in FIG. 1. It will be appreciated that some nodes in the AMI system 100, such as node 200A, may be located such that they receive messages from the collection hub 108 both directly and by way of one or more repeaters 114 or buddy nodes 200B.

The collection hub 108 and the repeater 114 are both shown including a long-range ("LoRa") frequency module (LFM) 111. The LFM 111 is a radio module mounted to a board that can be installed in the hub 108 and the repeater 114, and is intended to be compatible with radios inside nodes 200, including but not limited to LoRaWAN™ radio, and radios in node types sold by applicant under the names "MiNet.m" and "MiNode.m." In an AMR network, in which a collector (not shown) substitutes for hub 108, an LFM 111 could also be housed in the collector.

According to some embodiments, the collection hubs 108 may include or be connected to an accurate time source 118. For example, a collection hub 108 may be GPS-enabled and able to receive a highly accurate time value from a GPS receiver. Other accurate time sources 118 may include a cellular network connection, an integrated accurate real-time clock component, and the like. Because collection hubs 108 may be connected to fixed power sources, these devices may be able to maintain accurate current time without the need for reduced power consumption required by other, remote nodes 200. It will be appreciated that the configuration of the network comprising the AMI system shown in FIG. 1 and described above is merely one configuration, and additional devices and/or alternative configurations may be conceived by one skilled in the art. As such, the network topology shown in FIG. 1 and the network configurations described should not be seen as limiting but, instead, as merely exemplary.

The communication links shown in FIG. 1 represent a network or networks that may comprise hardware components and computers interconnected by communications channels that enable sharing of resources and information. The network may comprise one or more of a wired, wireless, fiber optic, or remote connection via a telecommunication link, an infrared link, a radio frequency link, a cellular link, a Bluetooth® link, or any other suitable connectors or systems that provide electronic communication. The network may comprise intermediate proxies, routers, switches, load balancers, and the like. The paths followed by the network between the devices as depicted in FIG. 1 represent the logical communication links between nodes (such as 200B and 200C), between a node 200 and the hub 108, or between nodes 200 and the repeater 114, not necessarily the physical paths or links between and among the devices.

Figure 2:
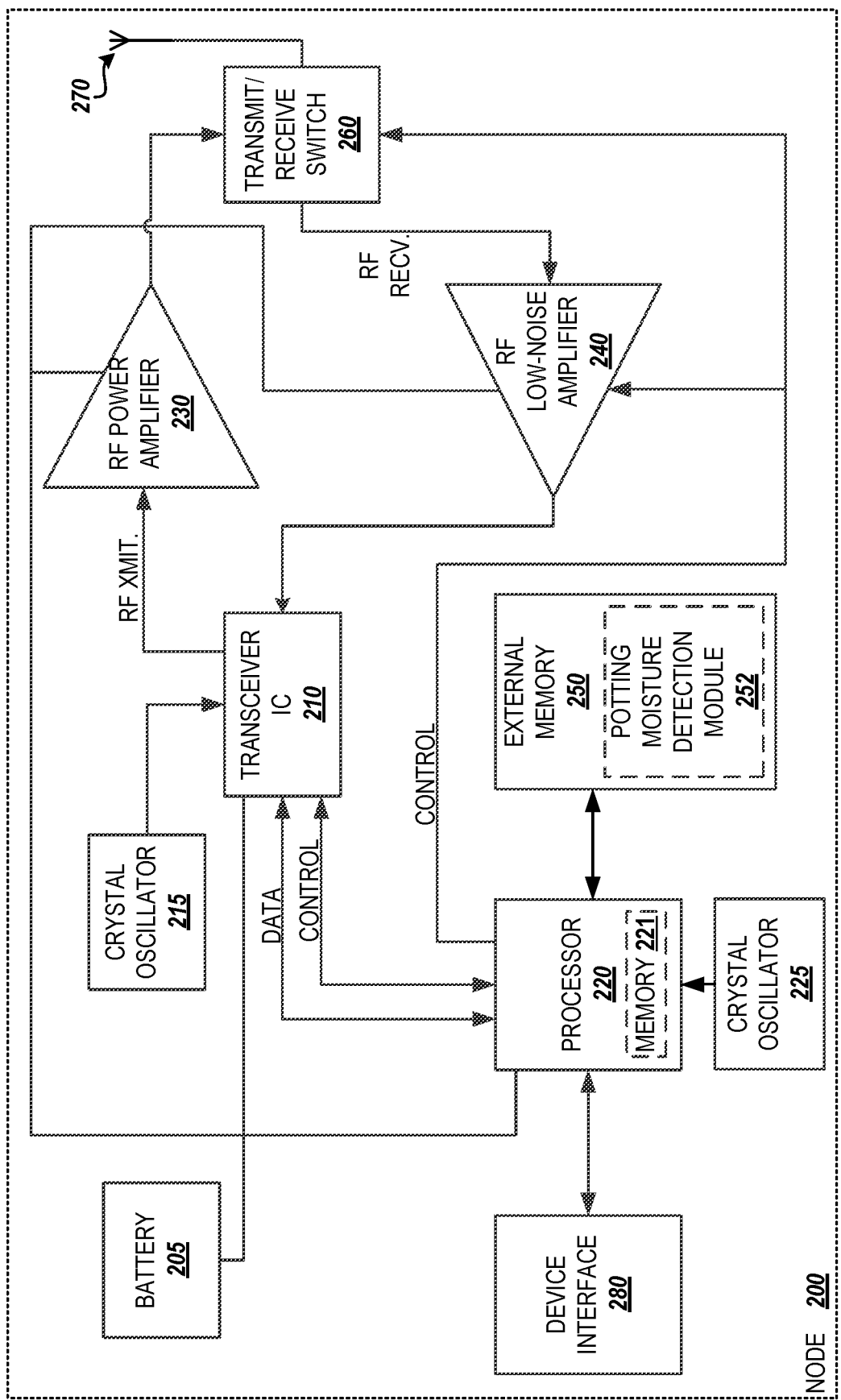
FIG. 2 is a block diagram of a node according to aspects of the present disclosure.

FIG. 2 shows a block diagram of components of an illustrative node 200 configured for RF communication in AMR and AMI networks. In other words, the node 200 is able to operate in an AMI mode or in a modified AMR mode (the latter mode described in application Ser. No. 15/161,448, filed May 23, 2016, and incorporated by reference above). The node 200 may allow data to and from devices in the AMI system 100, such as water, gas, or electrical meters, remotely controlled valves, flow nodes, leak detection devices, collection hubs 108, repeaters 114, and the like, to be communicated over the wireless AMI network. For example the node 200 may be implemented in or connected to a water meter in order to transmit usage data as well as, in some implementations, audio recording data to the host 102 for leak detection. According to various embodiments, the node 200 may be configured for communication on various radio network topologies, including star, hybrid-star, peer-to-peer, and mesh, among others.

The node 200 may include at least one battery 205 that powers a transceiver integrated circuit ("IC") 210, a processor 220 having a built-in memory 221, an RF power amplifier 230, an RF low-noise amplifier 240, a memory 250, and other components. In some implementations, processor 220 can be an 8/16-bit microcontroller sold by Atmel Corporation under the name "AVR XMEGA D3." Memory 250 is an "external" memory in the sense that it is separate from, and not contained within, another node component, unlike built-in memory 221, for example. References to "external" memory herein are intended to refer to memory of the configuration illustrated in FIG. 2 at 250. Other embodiments include nodes with fewer elements, e.g., nodes without power amplifiers or low noise amplifiers, among others. Crystal oscillators 215 and 225 are connected to the transceiver IC 210 and the processor 220, respectively. The node 200 further includes a transmit/receive switch 260 and antenna 270. The processor 220 may be a microprocessor, a microcontroller, a field-programmable gate array ("FPGA"), or the like. The processor 220 and the transceiver IC 210 may include both a two-way data and a two-way control line. In some embodiments, the processor 220 includes a control line to each of the RF low-noise amplifier 240 and the transmit/receive switch 260. The processor 220 may also be connected to the memory 250 by a two-way data line.

Figure 3:
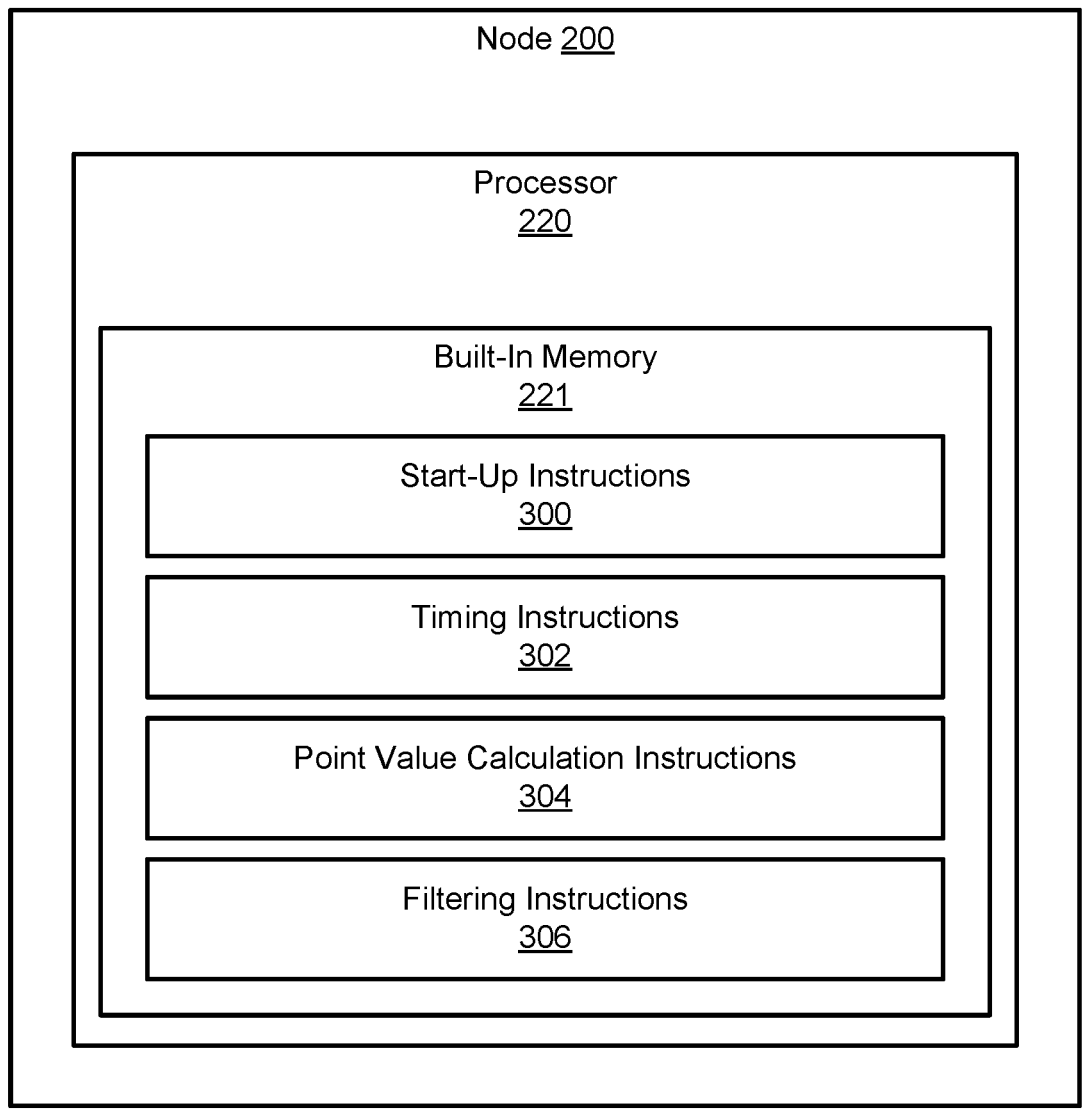
FIG. 3 is a block diagram depicting the various types of instructions stored in a non-transitory memory resource of an exemplary node according to aspects of the present disclosure, the instructions executable by the processor to detect moisture within a potting compound in the node.

The built-in memory 221 and external memory 250 may each comprise a processor-readable storage medium for storing processor-executable instructions, data structures and other information. The built-in memory 221 and external memory 250 may include a non-volatile memory, such as read-only memory ("ROM") and/or FLASH memory, and a random-access memory ("RAM"), such as dynamic random access memory ("DRAM") or synchronous dynamic random access memory ("SDRAM"). The built-in memory 221 and external memory 250 may store firmware that comprises commands and data necessary for the nodes 200, collection hubs 108, and repeaters 114 to communicate with other devices in the AMI system 100 as well as perform other operations of the nodes. In some embodiments, the external memory 250 may store a potting moisture detection module 252 comprising processor-executable instructions that, when executed by the processor 220, perform at least portions of the start routine 1500 in FIG. 15, and the timing routine 1600 in FIG. 16, including an algorithm 1618 (FIG. 17) for the "calculate point value" step of the routine 1600, as described herein. However, in other embodiments (such as illustrated in FIG. 3), the instructions comprising the potting moisture detection module 252, or parts thereof, may also be stored in either the built-in memory 221 or a combination of the built-in memory 221 and the external memory 250, each of the memory storage variations discussed in this paragraph encompassed within the term "memory resource" as used herein.

In addition to the memory 250, the node 200 may have access to other processor-readable media storing program modules, data structures, and other data described herein for accomplishing the described functions. It will be appreciated by those skilled in the art that processor-readable media can be any available media that may be accessed by the processor 220 or other computing system, including processor-readable storage media and communications media. Communications media includes transitory signals. Processor-readable storage media includes volatile and non-volatile, removable and non-removable storage media implemented in any method or technology for the non-transitory storage of information. The memory resource of the present disclosure is non-transitory in the sense that it does not encompass a transitory signal but instead is made up of one or more memory components configured to store computer-executable (processor-executable) instructions. For example, processor-readable storage media includes, but is not limited to, RAM, ROM, erasable programmable ROM ("EPROM"), electrically-erasable programmable ROM ("EEPROM"), FLASH memory or other solid-state memory technology, compact disc ROM ("CD-ROM"), digital versatile disk ("DVD"), high definition DVD ("HD-DVD"), BLU-RAY or other optical storage, magnetic cassettes, magnetic tape, magnetic disk storage or other magnetic storage devices and the like.

According to embodiments, the processor 220 may be further connected to other components of the node 200 through a device interface 280. In some embodiments, the device interface 280 may connect to a metering component, such as a water meter (exemplified in FIG. 1 at 22C, 22A, and 22D), a gas meter, or an electricity meter, that allows the meter to provide usage data to the host 102 through the AMI system 100. In further embodiments, the device interface 280 may connect to nodes or detection components, such as a leak detection device. In still further embodiments, the device interface 280 may connect to a control component, such as an electronically actuated water valve, that allows the host 102 and/or other devices in the AMI system 100 to control aspects of the utility provider's infrastructure. These examples are not meant to be limiting, and those of skill in the art will recognize that alternative device components that may be interfaced with the node 200 through the device interface 280. For example, the device interface 280 may connect to a control component (valve actuator) and a data reading port (water meter readings) at the same time.

It will be appreciated that the structure and/or functionality of the node 200 may be different than that illustrated in FIG. 2 and described herein. For example, the transceiver IC 210, processor 220, RF power amplifier 230, RF low-noise amplifier 240, memory 250, crystal oscillators 215, 225, device interface 280 and other components and circuitry of the node 200 may be integrated within a common integrated circuit package or distributed among multiple integrated circuit packages. Similarly, the illustrated connection pathways are provided for purposes of illustration and not of limitation, and some components and/or interconnections may be omitted for purposes of clarity. It will be further appreciated that the node 200 may not include all of the components shown in FIG. 2, may include other components that are not explicitly shown in FIG. 2, or may utilize an architecture completely different than that shown in FIG. 2.

It should also be understood that other devices within AMI network 100 such as, for example, hub 108 (FIG. 1) can be implemented in hardware and software in a manner similar to that of the node 200, with the understandable programming and hardware differences required to be in accordance with the processes discussed herein.

FIG. 3 is a block diagram of depicting various types of instructions 300, 302, 304, 306 stored in the non-transitory built-in memory 221 of an exemplary node 200 according to aspects of the present disclosure, the instructions 300, 302, 304, 306 executable by the processor 220 to detect moisture within a potting compound in the node 200. More particularly, in some implementations, the built-in memory 221 may have stored thereon start-up instructions 300 implementing the method 1500 to be discussed herein with regard to FIG. 15, timing instructions 302 implementing the method 1600 to be discussed herein with regard to FIG. 16, point value calculation instructions 304 implementing the method 1618 to be discussed herein with regard to FIG. 17, and filtering instructions 306 to be discussed herein with regard to FIG. 13. Such computer-executable programming instructions can be stored in any of the disclosed non-transitory memory resource varieties and run on the same or different microprocessors and/or computer systems.

FIGS. 4-8 disclose various views of a circuit board assembly 400, including a circuit trace connecting a test point to a processor pin (FIG. 6), in relation to a housing 500 of the node 200, prior to depositing any potting compound within the housing 500.

Figure 4:
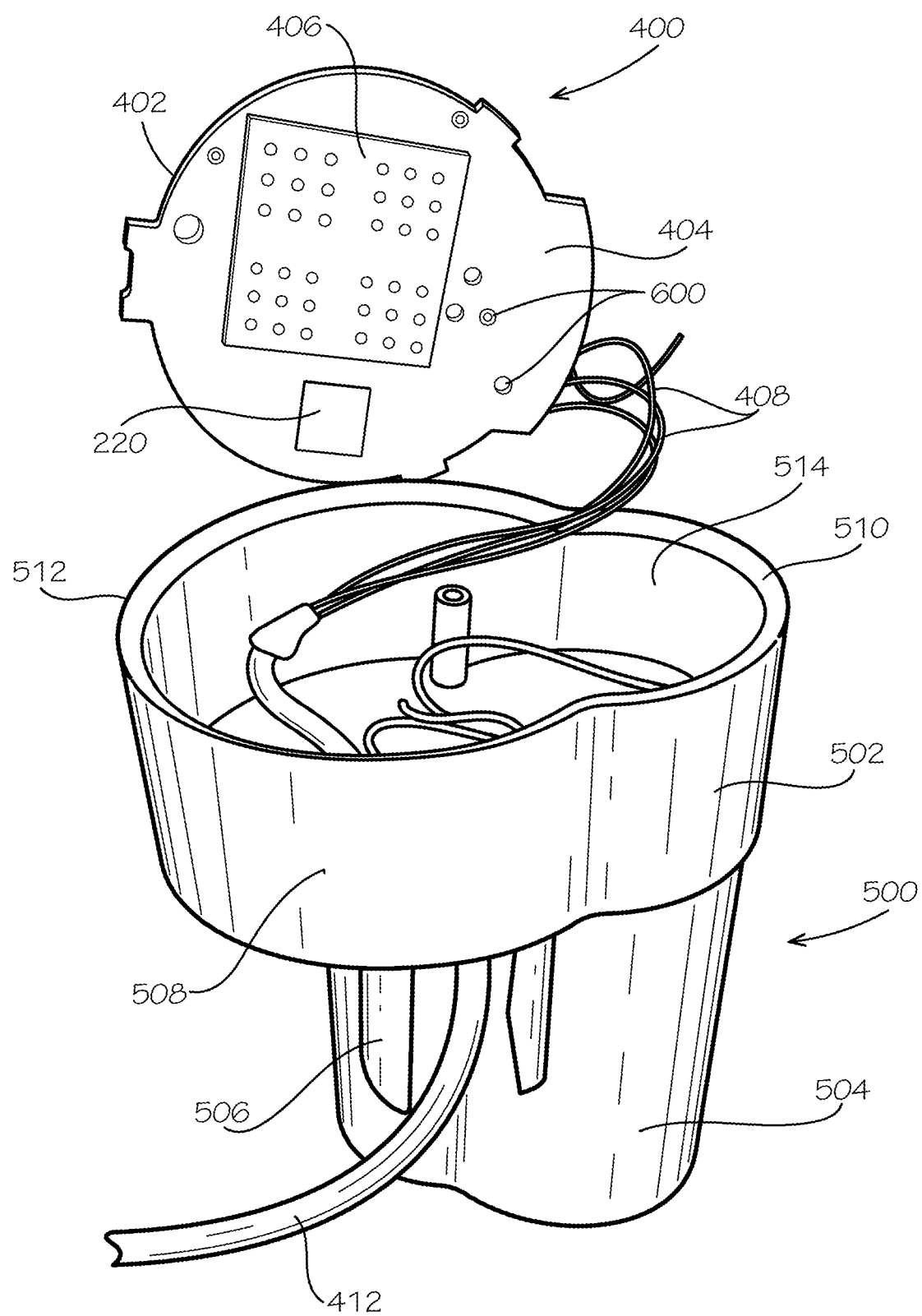
FIG. 4 is a perspective view of a node housing and of the underside of a circuit board assembly configured for placement within the housing, according to certain embodiments described herein.
Figure 5:
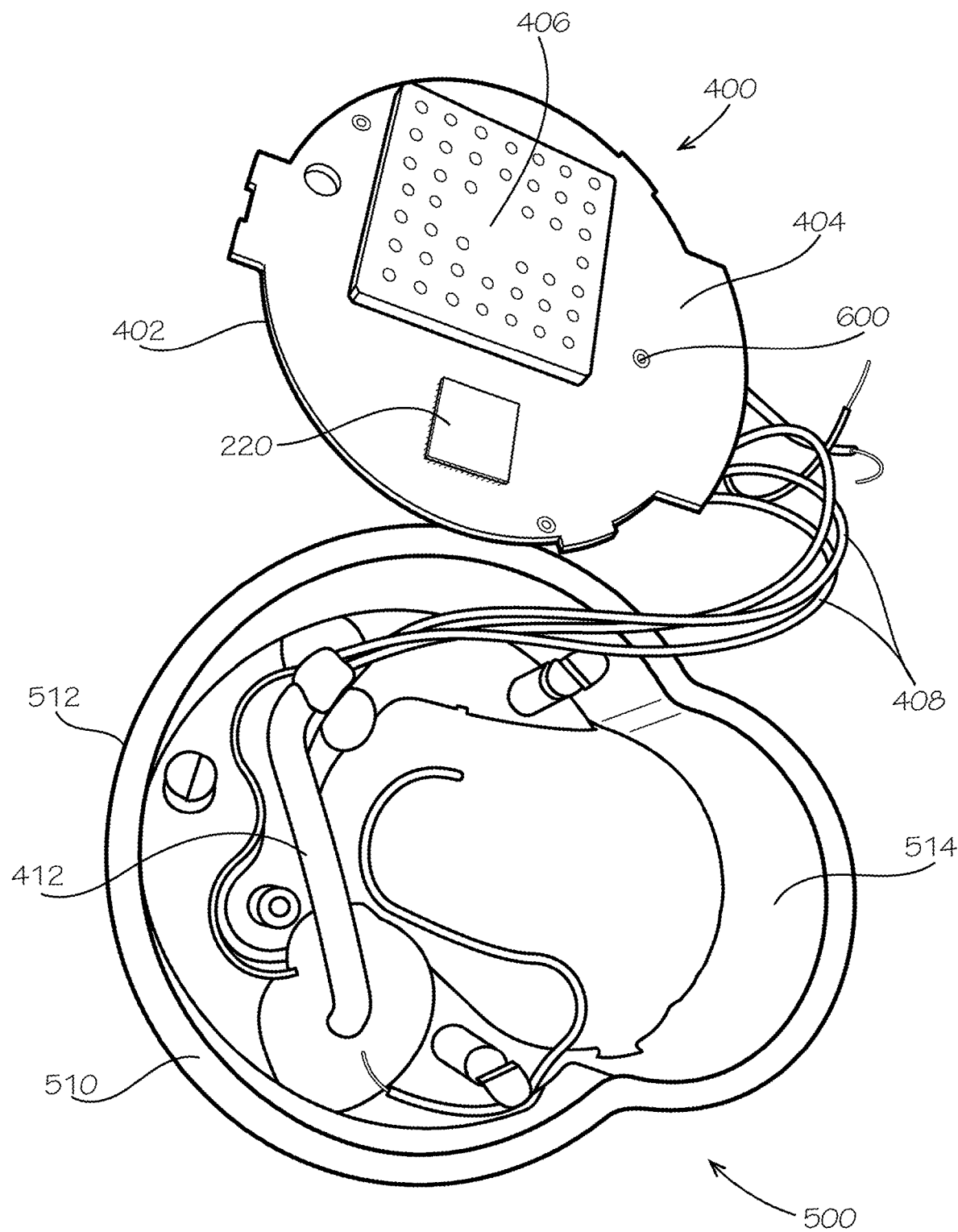
FIG. 5 is a top view of the node housing, and a top perspective view of the underside of the circuit board assembly, illustrated in FIG. 4, showing a plurality of test points in the circuit board of the circuit board assembly proximate a processor mounted to the circuit board.

Referring to FIGS. 4 and 5, circuit board assembly 400 includes a circuit board 402 having an underside (bottom) surface 404, on which are mounted the processor 220 and a shield 406 designed to protect other components (not shown) mounted to the underside circuit board surface 404. A plurality of test points 600 can be formed into the underside circuit board surface 404, at least one of them electrically communicating with the processor 220 in the manner to be described herein with regard to FIG. 6. A plurality of wires 408 are connected to the top surface 405 of the circuit board 402 via corresponding connectors 410 (FIG. 7). Three of the wires 408 form a cable 412 that can be routed from the housing 500 to a utility device, including a water meter, such as any of water meters 22A, 22C, 22D (FIG. 1). Housing 500 can be a unitary, single-piece structure constructed of any suitable material known in the art, such as plastic. Housing 500 can comprise an upper section 502, a lower section 504 extending downwardly from the upper section 502, and a conduit section 506 extending downwardly from the upper section 502 frontwardly of the lower section 504. Conduit section 506 is seen protecting a portion of the cable 412. Upper section 502 can define a wall 508 forming a rim 510 at its upper end, the rim 510 terminating upwardly at a ridge 512. Wall 508 can also define a cavity 514 within the upper section 502 of the housing 500.

Figure 6:
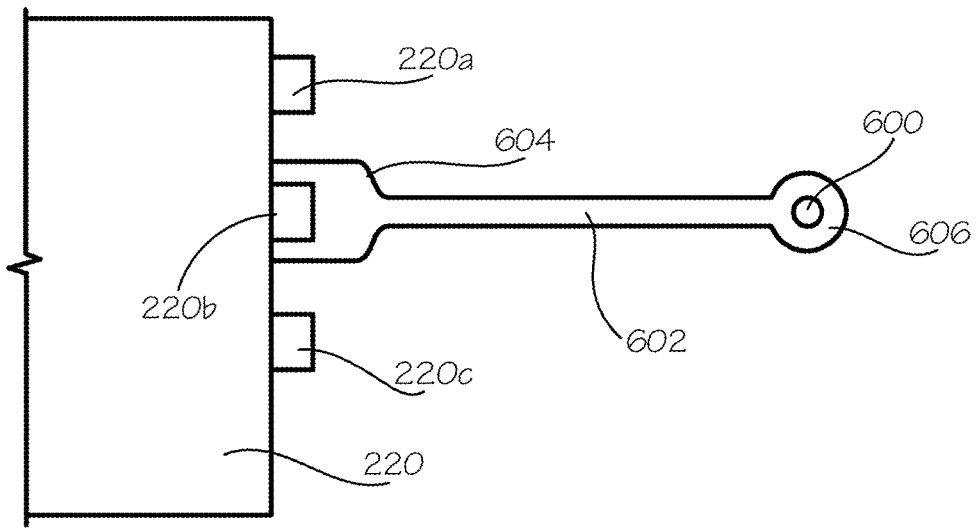
FIG. 6 is a schematic diagram illustrating electrical communication between a pin on the processor illustrated in FIG. 5 and a test point formed into the circuit board of the circuit board assembly illustrated in FIG. 5.
Figure 7:
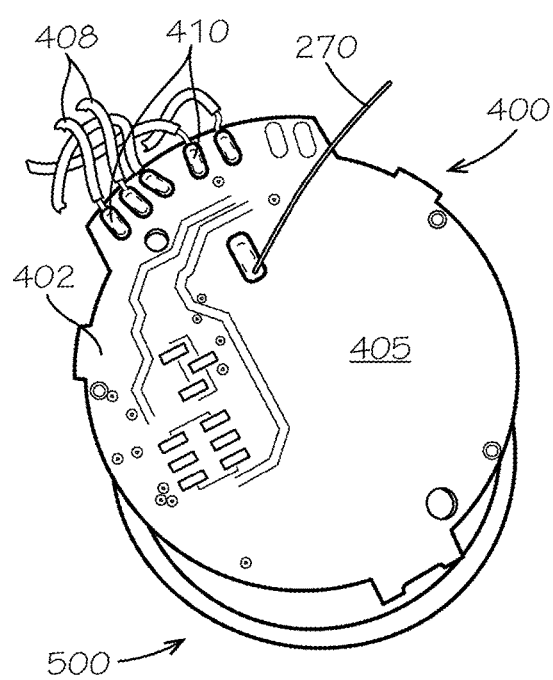
FIG. 7 is a top view of the top side of the circuit board assembly illustrated in FIG. 4.

FIG. 6 is a schematic diagram illustrating electrical communication between a pin 220b on the processor 220 and a test point 600 formed in any conventional manner into the underside circuit board surface 404 (FIGS. 4 and 5). Processor 220 can comprise a plurality of pins such as those exemplified at pins 220a,b,c. A trace 602, formed of electrically conductive material, can be deposited onto the underside circuit board surface 404 in any conventional manner, one end of the trace 602 forming a pad 604 contacting pin 220b, and the opposed end of the trace forming a circular section 606 encircling the test point 600. Trace 602 thereby can provide electrical communication between the test point 600 and the processor 220 via pin 220b.

Figure 8:
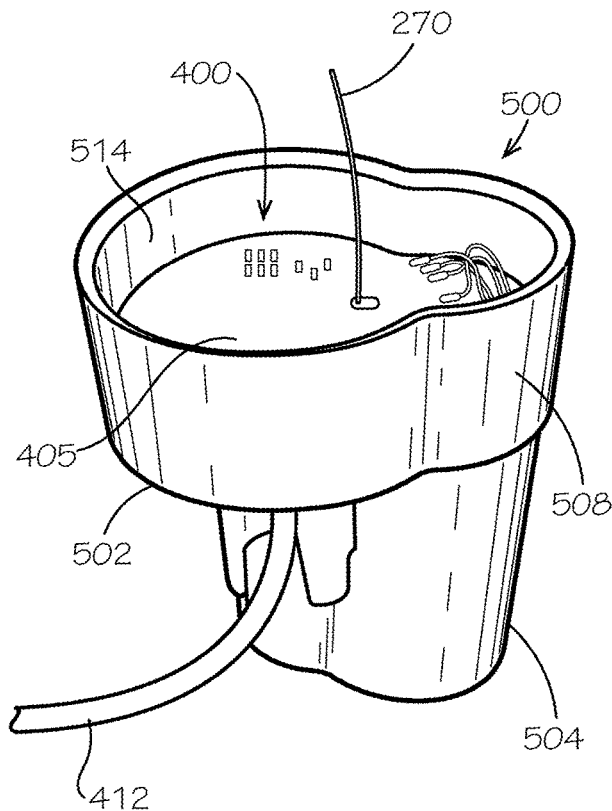
FIG. 8 is a perspective view of the node housing and circuit board assembly shown in FIG. 4, with the circuit board assembly shown seated within the housing.

Referring to FIGS. 7 and 8, the top circuit board surface 405 is seen to carry antenna 270 (also shown schematically in FIG. 2), which enables the node 200 to wirelessly communicate with other system elements in the manner described above with regard to FIG. 1. As best seen in FIG. 8, the shape of the circuit board 402 can be configured to permit the circuit board assembly 400 to be snugly received into the cavity 514 of the housing upper section 502.

Figure 9:
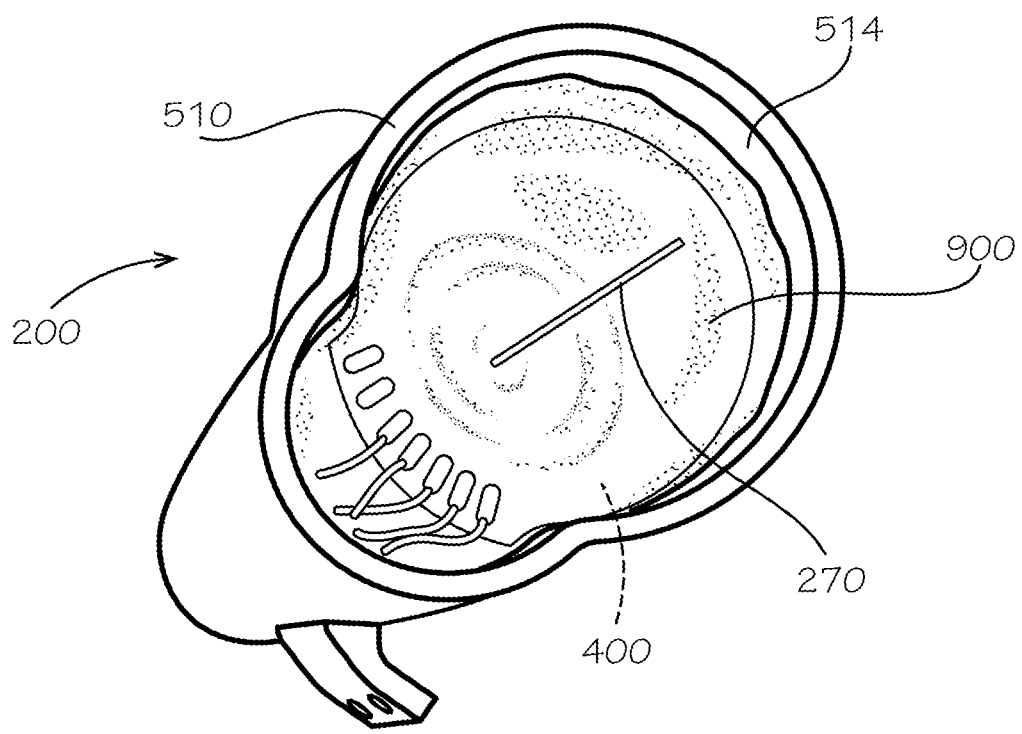
FIG. 9 is a top view of a node, showing the circuit board assembly illustrated in FIG. 4 submersed into clear potting compound deposited within a cavity defined by the node housing illustrated in FIG. 4.
Figure 10:
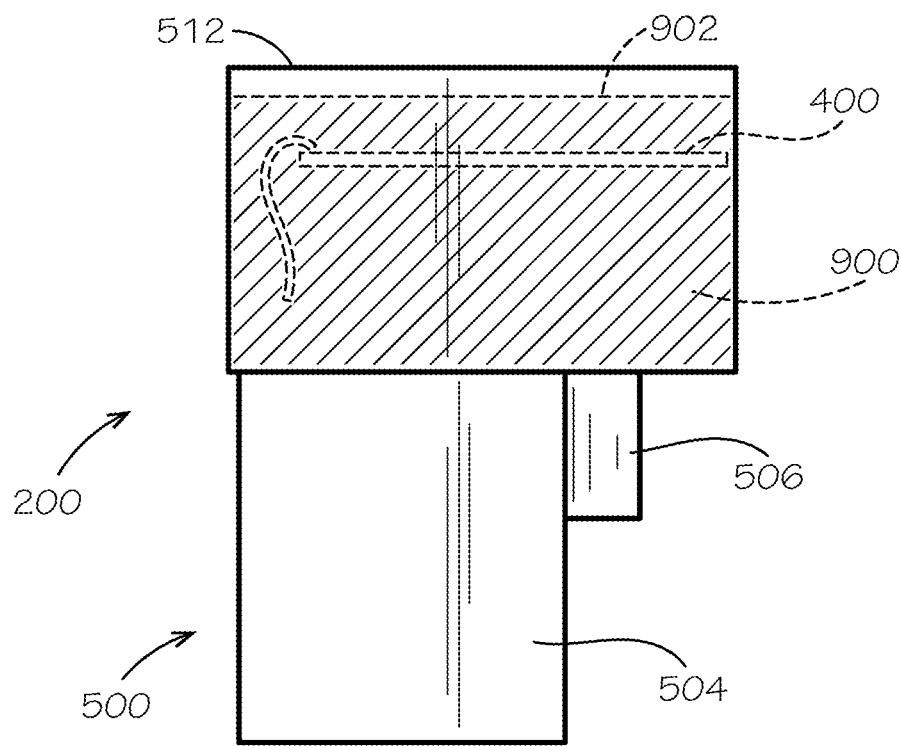
FIG. 10 is a side view of the node illustrated in FIGS. 8 and 9, with its internal elements shown in phantom lines.

FIGS. 9 and 10 depict a complete node 200, showing the circuit board assembly 400 submersed into a clear potting compound 900 deposited within the cavity 514 of the node housing 500. When the node 200 is assembled, the circuit board assembly 400 is positioned inside the housing 500, above the node battery 205 (FIG. 2, not shown here). In some implementations, potting compound 900 is then poured over the battery 205 and the circuit board assembly 400 until the circuit board 402 is roughly half an inch deep in the potting compound 900, i.e., ½" below the top surface 902 of the potting compound 900.

Figure 11:
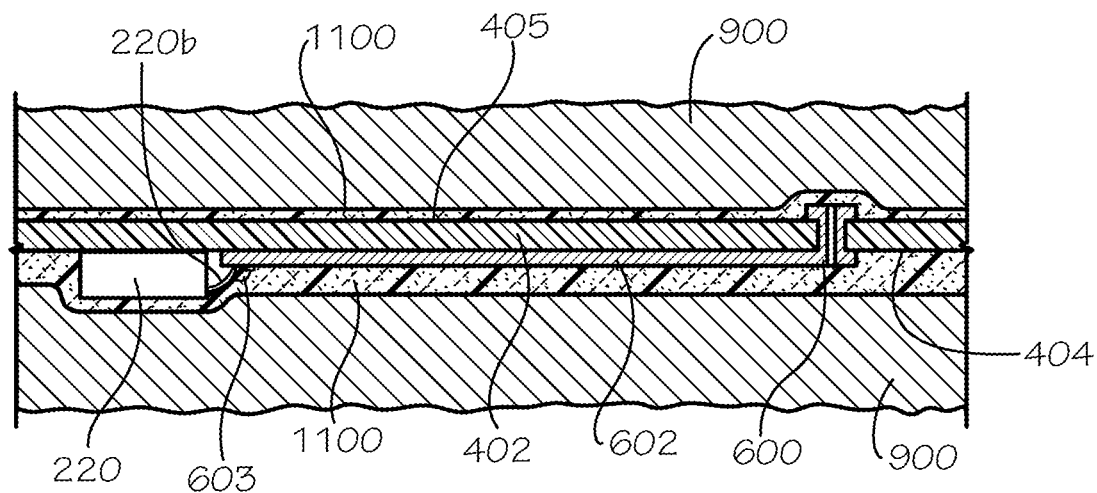
FIG. 11 is a side sectional view illustrating the spatial and communicative relationships between the processor pin and the test point illustrated in FIG. 6, and layers corresponding to a circuit board, a circuit board trace, an insulating material, and a potting compound.
Figure 12:
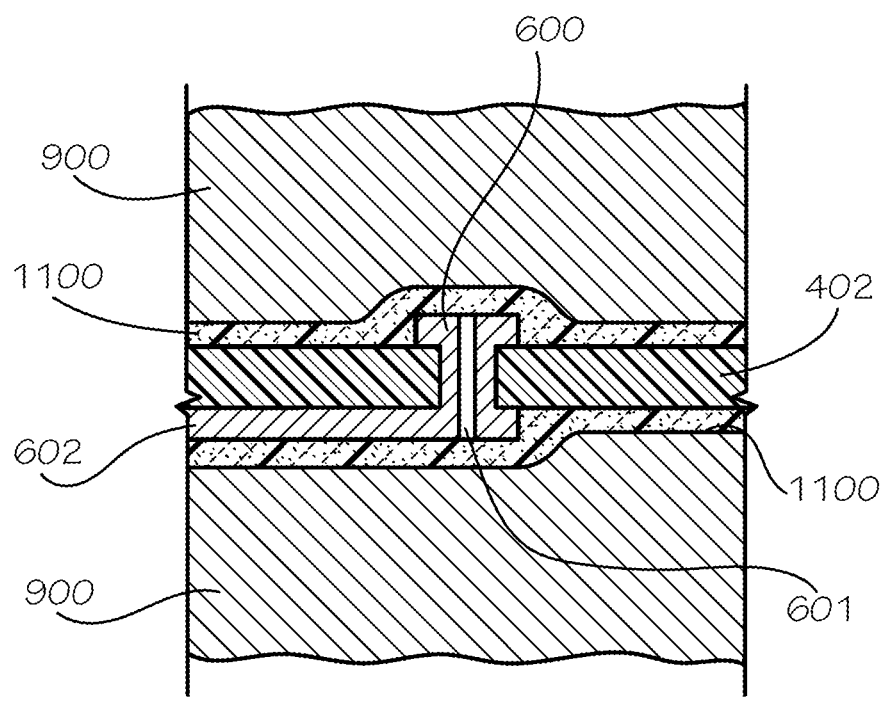
FIG. 12 is an enlarged side sectional view of the called-out portion of FIG. 11.

FIGS. 11 and 12 are side sectional views illustrating the spatial and communicative relationships between the processor pin 220b of processor 220 and the test point 600, and layers corresponding to the circuit board 402, trace 602, an insulating material ("insulator") 1100, and the potting compound 900. Test point 600, which may comprise the same conductive material as trace 602, can be seen in FIG. 12 as having a bore 601, designed to accommodate a pin from a device that performs a board level test of the circuit board assembly 400 during its manufacture and prior to application of any insulating material 1100. Pin 220b of the processor 200 can be physically and electrically connected to the trace 602 at solder 603. As shown in FIG. 11, and as also shown in FIG. 6, the test point 600 can electrically communicate with solder 603, and thus with pin 200b, via the trace 602. The insulator 1100, applied after completion of the board level test, can cover the test point 600, the trace 602, and the solder 603, as well as the top surface 405 and the bottom surface 404 of the circuit board 402, leaving exposed only connections for a power supply (not shown) and a water meter (such as at 22A,C,D of FIG. 1). The insulator 1100 can be a polymeric material used as both a moisture and dielectric barrier to protect and electrically insulate trace 602 and the test point 600, and in some implementations may be commercially-available from Specialty Coating Systems, Inc. (Indianapolis, Ind.) under the trademark PARYLENE HT®.

Figure 13:
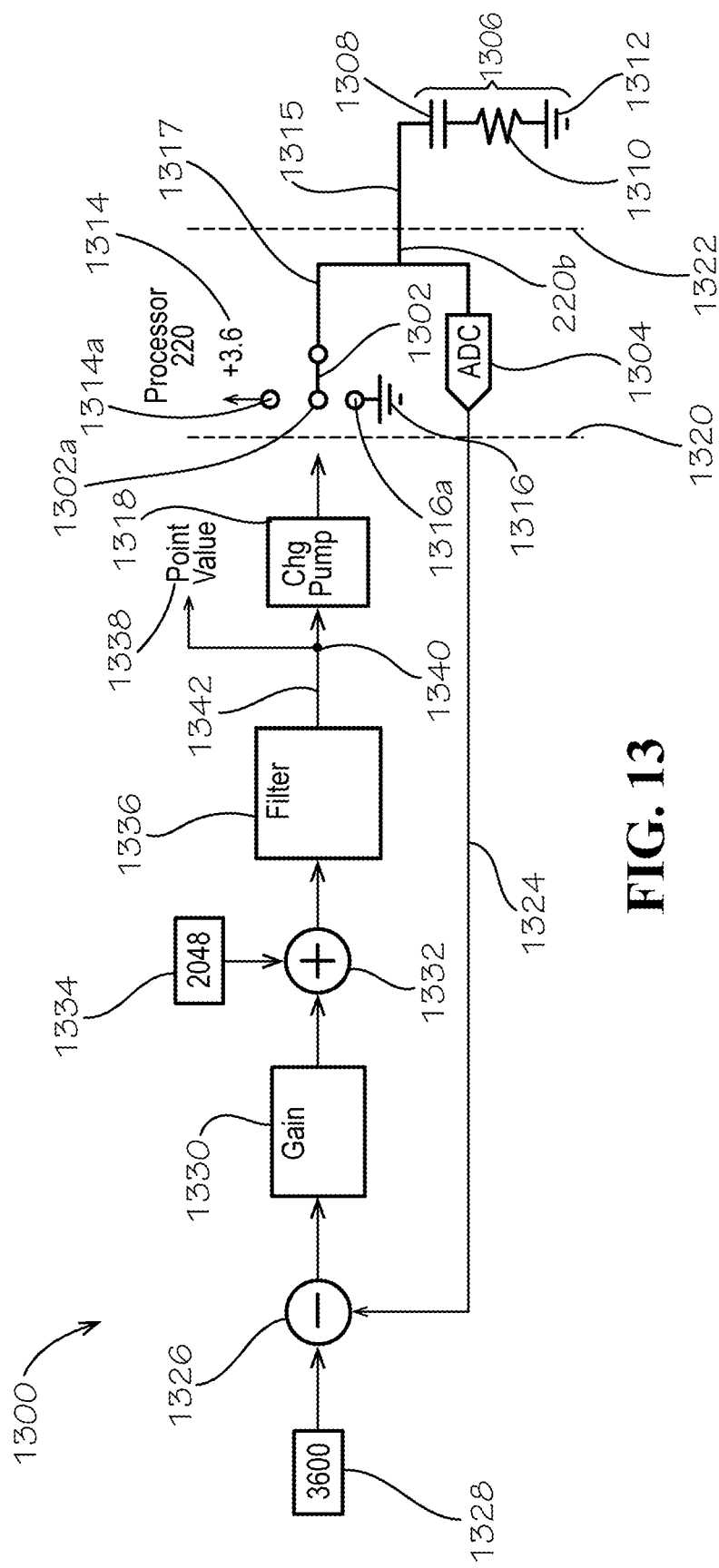
FIG. 13 is a schematic diagram illustrating a closed-loop potting moisture detection system according to aspects of the present disclosure, illustrating relationships among programming elements, a processor switch, an analog-to-digital converter inside the processor, and an equivalent resistor-capacitor ("RC") circuit, external to the processor, formed by the combination of potting compound and insulator material at the test point illustrated in FIGS. 6 and 11.

FIG. 13 is a schematic diagram illustrating a closed-loop potting moisture detection system 1300 according to aspects of the present disclosure, illustrating relationships among programming elements, a processor switch 1302, an analog-to-digital converter ("ADC") 1304 inside the processor 220, and an equivalent resistor-capacitor ("RC") circuit 1306, external to the processor 220, formed by the combination of the potting compound 900 and the insulator 1100 at the test point 600 (FIGS. 11 and 12). It has been found that the insulator 1100 acts as an equivalent capacitor 1308, and that the potting compound 900 acts as an equivalent resistor 1310, the equivalent RC circuit 1306 being grounded at 1312 as shown. At least in implementations where the processor 220 is the aforementioned Atmel® microcontroller, the processor 220 includes a switch 1302, the illustration of which in FIG. 13 conceptually represents a tri-state buffer switch that is configured to selectively assume a first position, a second position, and a third position. Switch 1302 can comprise transistors (MOSFETS), which are current sources that output lines of constant current. One transistor pulls voltage on a processor port high when it is turned on, while another transistor pulls the port low when the switch 1302 goes to ground. The first position, in which switch terminal (or end) 1302a of the switch 1302 contacts a terminal 1314a of a voltage source 1314, brings the equivalent RC circuit 1306 into electrical communication with the voltage source 1314. FIG. 13 depicts the voltage source 1314 at 3.6V, but this disclosure is not limiting, and other suitable values may be used in other implementations. The second position, in which switch terminal 1302a assumes the position depicted in FIG. 13, results in an open circuit between the voltage source 1314 and the equivalent RC circuit 1306. The second position is known as a "High-Z," or high-impedance, state resulting from a logic level being applied to an "enable" control line (not shown) of the switch 1302. For example, if switch 1302 is an active-high tri-state buffer switch, a logic level "0" will cause a high-impedance state in the switch 1302, in which it draws no current, and its output is disabled. The third position, in which the switch terminal 1302a contacts a ground terminal 1316a of an electrical ground 1316, brings the equivalent RC circuit 1306 into electrical communication with the electrical ground 1316. Computer-executable instructions, when executed by the processor 220, cause the processor 220 to selectively bring the switch 1302 into one of the first position, the second position, and the third position. Such instructions are herein referred to as a "charge pump," represented in block form at 1318. It is noted that in FIG. 13, a dashed vertical line 1320 conceptually separates the hardware elements of processor 220 from software instructions (including the charge pump 1318), and that dashed vertical line 1322 demarcates a boundary between the hardware elements of processor 220 and the external hardware elements comprising the equivalent RC circuit 1306 and associated connections.

Responsive to the charge pump 1318, the processor 220 implements a switching sequence between the first, second, and third positions to result in a pulse train, described below with regard to FIGS. 14A and 14B. The pulse train is delivered to the equivalent RC circuit 1306 at the test point 600 (FIGS. 11 and 12), since the test point 600, and thus the equivalent RC circuit 1306, electrically communicates with the processor 220 via a first electrical path 1315 formed by the trace 602, pad 604, and pin 220b (FIGS. 11 and 12), and since a second electrical path 1317 within the processor 220 brings switch 1302 into electrical communication with the first electrical path 1315. Thus, the actions of charge pump 1318 and switch 1302 apply electrical charge to the equivalent RC circuit 1306, at the test point 600, in the form of a pulse train. Charge is applied in that manner because the equivalent RC circuit 1306 has been found to respond in a measurable voltage (as will be discussed herein) only when stimulated by rapidly varying the voltage or current. The capacitance of the equivalent capacitor 1308 has been found to be very small (on the order of 1 to 2 picofarads, i.e., (1 to 2)×$10^{-12}$ F. Because of such small capacitance, the equivalent capacitor 1308 can only be charged by a time-varying voltage/current waveform. By contrast, the resistance of the potting compound (represented by equivalent resistor 1310) is quite large, on the order of $10^7$ to $10^{100}$ ohms ($\Omega$), determined in one exemplary instance to be approximately $10^8\Omega$. The equivalent RC circuit 1306 responds exponentially to charge stimulation (charge is put into the equivalent RC circuit 1306 via the charge pump 1318), and thus the control loop formed by the system 1300 exaggerates (slows and amplifies) the response of the equivalent RC circuit 1306 for measurement. The order of magnitude of the equivalent capacitor 1308 can be deduced experimentally by measuring applied charge and resulting test point voltage, and using the equation C=q/V, discussed in another form below. With a value of "C" known, one can then find the equivalent resistance R by solving for it using the differential equation describing the response of an RC circuit with a voltage source in the circuit:

$$V(t)=Vi*e^{\hat{}}(-t/RC),$$

Where
Vi is initial capacitor voltage,
e is base of natural logarithm,
t is time, and
RC is the product of the resistor and capacitor values.

It can be shown that the voltage across the equivalent RC circuit 1306 decays in this situation to 90% of initial value in about T(90%)=3*RC. This is known as three time constants. Given the above magnitudes of "R" and "C," the equivalent RC circuit 1306 can hold a charge for T=RC= ($10^8\Omega$)×($10^{-12}$ F)=approximately $10^{-4}$ seconds. This is about 100 micro seconds. As said above, the purpose of the control loop is to exaggerate and slow this effect for measurement. A measurement (point) represents the voltage on the equivalent capacitor 1308 at the test point 600 after applying charge to the equivalent RC circuit 1306 with the charge pump 1318. The test point voltage V=q/C, where:
C is capacitance (in Farads),
q is charge (in Coulombs), and
V is the test point voltage.

Since the equivalent capacitor 1308 and the equivalent resistor 1310 are in series, the charge that is pumped into the equivalent capacitor 1308 also goes through the potting resistance (equivalent resistor 1310). Therefore, the RC time constant is a strict function of the resistance of the potting compound 900, because the capacitance (C) remains constant for a given circuit board and voltage source 1314. The test point voltage V is thus a measure of the charge responsive to a charge pump stimulus.

Figure 14A:
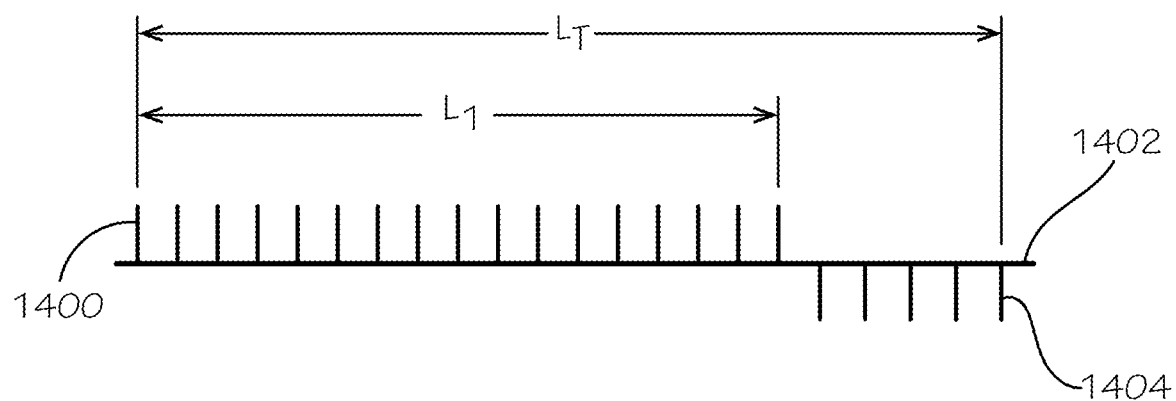
FIGS. 14A and 14B are pulse diagrams illustrating examples of operation of a charge pump in the potting moisture detection system illustrated in FIG. 13.
Figure 14B:
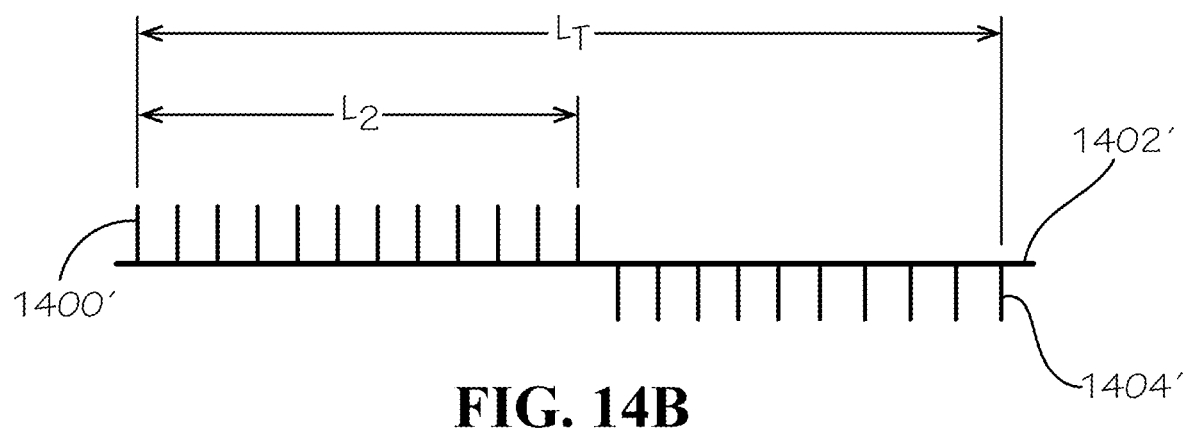

FIGS. 14A and 14B are pulse diagrams illustrating examples of operation of the charge pump 1318 of FIG. 13. In these diagrams, high pulses 1400,1400' correspond to the first position of the switch 1302, and each high pulse represents a magnitude of voltage equal to the voltage supplied by the voltage source 1314 (FIG. 13). Thus, in implementations of the example of FIG. 13, each high pulse has a magnitude of 3.6V. The positions 1402,1402' correspond to the second position of the switch 1302, reflecting the "Hi-Z" state of the switch 1302 described above with regard to FIG. 13. The "Hi-Z" state is not equal to a logic high (such as 3.6V) or a logic low (such as 0V); instead, the "Hi-Z" state results in an open circuit voltage between circuit elements equal to whatever voltage may exist in the equivalent RC circuit 1306 at the moment the "HI-Z" state occurs. The low pulses 1404,1404' correspond to the third position of the switch 1302; since that position represents a connection to ground 1316 (FIG. 13), the low pulses 1404, 1404' represent a magnitude of zero volts. Each pulse (whether high or low) preferably has the same duration (50 μs in some implementations). Furthermore, the duration of each interval between each pulse, i.e., the time at which the switch 1302 is at position 1402,1402', is likewise the same (3 ms in some implementations). The examples of FIGS. 14A and 14B are intended to reflect the use of the same ADC 1302 in the processor 220 (FIG. 13), so the total pulse train length $L_T$ is the same for both FIGS. 14A and 14B. In the example of 14A, the pulse train has a length $L_1$ of high pulses 1400 that is three-quarters (¾) of the total length $L_T$ of the entire pulse train. In the example of FIG. 14B, the pulse train has a length $L_2$ of high pulses 1400' that is half (½) of the total length $L_T$ of the entire pulse train. In such examples, the length $L_1$, $L_2$ of the high pulses 1400,1400', respectively, is proportional to a magnitude of electrical charge to be applied to the test point 600. Thus, a greater amount of electrical charge is applied to the test point 600 in the example of FIG. 14A than in the example of FIG. 14B. Regarding the relationship between the high pulse lengths $L_1$, $L_2$ and the different magnitudes of applied charge, the charge pump 1318 is a subroutine called with a numeric value from the output of a filtration routine 1336 (FIG. 13) in the closed loop system 1300. The output from that filtration routine 1336 is a filtered value that is ultimately derived from the ADC value, as explained in detail below. In some implementations, the ADC 1302 has a maximum input voltage capacity of 1V, which corresponds to a ratiometric value (reading) of the numeral 4096. With such implementations, the value 4096 corresponds to a pulse train that would comprise all high pulses 1400,1400'. In such a hypothetical instance, referring to FIG. 14A, $L_1$ would equal $L_T$. Thus, for instance, inputting ¾ of the value 4096 (=3072) into the charge pump 1318 would produce the pulse train of FIG. 14A, while inputting ½ the value of 4096 (=2048) into the charge pump 1318 would produce the pulse train of FIG. 14B. As a result, the amount of charge applied to test point 600 is a function of the ADC-related numeric value input into the software subroutine represented as the charge pump 1318, and the greater that numeric value, the proportionally greater the applied charge. Using the combination of high and low pulses as exemplified in FIGS. 14A and 14B maintains uniformity of the time taken to apply charge to the test point 600. Despite the differing amounts of charge represented in those figures, the time taken to apply those charges, i.e., the total time length of operation of the charge pump 1318, is the same. This keeps the full loop operation time a constant period, preventing a time lag variable from being introduced into the closed-loop potting moisture detection system 1300 of FIG. 13, which thereby also prevents system instability that would otherwise result from time lag variances.

Referring again to the closed-loop potting moisture detection system 1300 of FIG. 13, the process of determining relative moisture content in the potting compound of a node begins with an initial iteration of applying electrical charge to the equivalent RC circuit 1306 at test point 600, in the manner described above. In that initial iteration, the value input into the charge pump 1318 can be 2048, which is half the capacity of the ADC 1304 exemplified above. The value 2048 was chosen as the midpoint value to allow for variances in conductance of the equivalent RC circuit 1306, which was found to exhibit lower conductances in warmer, drier ambient conditions. Lower conductances produce higher voltage readings following application of charge. While 2048 was found to be a suitable initial value to input into the charge pump 1318, that disclosure is not meant to be limiting, and other initial values that account for low-conductance conditions are contemplated as being within the scope of the present disclosure. After lapse of a predetermined delay period following the application of electrical charge to the test point 600 in the manner described above, with the delay period in some implementations ranging from, for example, 100 microseconds (μs) to 10 milliseconds (ms) (with 500 μs being an example of a delay within that range), the ADC 1304 is commanded to read a test point voltage at the test point 600. The stated range for the delay period is provided merely as an example for illustrative purposes and is not intended to be limiting. The command to the ADC 1304 comes from a central processing unit (CPU) (not shown) in the processor 220. After the aforementioned delay period, software in the CPU will send a signal along an electrical line, or bus (also called a "Processor Hardware Line") running from the CPU to the ADC 1304, the bus also electrically communicating with a processor pin (such as pin 220a in FIG. 6). The CPU puts its commands on the bus, and the ADC 1304 will take signals off of the bus, one of which is a command to convert an input voltage (here, the test point voltage) to a numeric value (the ADC value). When the ADC 1304 executes that command, the ADC 1304 produces, at its output, a ratiometric numeric value (hereinafter "the ADC value") corresponding to the test point voltage read by the ADC 1304, and puts the ADC value on the bus, from which the CPU retrieves the ADC value and stores that value into a memory to initiate processing of that value within the CPU's registers in the manner described herein. The ADC 1304 can read a test point voltage because the second electrical path 1317 is routed into the input of the ADC 1304, such that the ADC 1304, like the second electrical path 1317, electrically communicates with the first electrical path 1315 and thus with the equivalent RC circuit 1306 at the test point 600.

Still referring to FIG. 13, as depicted by servo loop arrow 1324, the ADC value is fed into a subtraction routine 1326, where an offset value 1328 is subtracted from the ADC value. The offset value 1328 is a number entered into the programming for subtraction routine 1326 that corresponds to an ambient voltage at the test point 600. Also called a "rest voltage," the term "ambient voltage" as used herein refers to voltage measured at the test point 600 before any application of electrical charge to it by the charge pump 1318. In the example of FIG. 13, the offset value 1328 is 3600 because in repeated measurements, 3600 was the average ADC reading of the ambient voltage of the potting compound/insulator combination in a node prior to application of any charge to it. However, the disclosure of 3600 as the offset value 1328 is not meant to be limiting, and other magnitudes for the offset value 1328 could be used, and can vary with differing types of ADCs implemented as the ADC 1304. A node 200 constructed according to the present disclosure could have its ambient voltage determined upon completion of its assembly at a factory. In particular, a completed node 200 could be subjected to a calibration program initiated via a communication sent over a serial connection or sent wirelessly. Once the calibration routine begins, the ADC 1304 can be read "n" times. All readings can then be added together, then divided by "n" to obtain an average ADC value. That average value could then be stored in non-volatile memory (NVM), such as an EEPROM in the memory resource of the processor 220, as the offset value 1328 for reading by the system 1300 during operation, as described above. In such an arrangement, the subtraction routine 1326 would retrieve whatever value is stored in the NVM as the offset value 1328, instead of using a pre-programmed constant. Such pre-storage of the offset value 1328 in the NVM presents possible advantages in allowing for a self-calibrating system that is tied to the particular type of ADC being used, and in improving accuracy of deriving each point value 1338, discussed below. Another method of deriving and storing an offset value 1328 into the NVM can be for a customer to take ADC readings of several dry example nodes of the same type, and possibly also of the same stock (verified such as through use of date codes), as the networked node 200 to be measured by closed-loop potting moisture detection system 1300. The average ADC value from those example nodes could then be sent wirelessly to that node 200 by the customer (via network elements such as the host 102 or the hub 108 (FIG. 1), whereupon the value received by the node 200 is stored in its NVM for subsequent use in the subtraction routine 1326.

Subtraction of the offset value 1328 in FIG. 13 results in a corrected value, which is then sent to a gain routine 1330 that multiplies the corrected value by a gain factor to produce an attenuated value. In some implementations, the gain factor can be 0.67, although other suitable magnitudes for the can factor can be used. The purpose of the gain routine 1330 is to produce a waveform that can be read; waveforms with unacceptably large gains cannot be measured without great difficulty. The attenuated value is then sent to a summing routine 1332, which adds an initial state value 1334 to the attenuated value to produce a calibrated value. This ensures that any change in voltage within the equivalent RC circuit 1306 is measured relative to a baseline, i.e., the initial state value 1334. The initial state value 1334 corresponds to the first magnitude of electrical charge applied to the test point 600, i.e., the value input into the charge pump 1318 in the first iteration of applying charge to the equivalent RC circuit 1306. As discussed above, and as reflected in FIG. 13, that initial state value is 2048. Next, the calibrated value resulting from summing routine 1332 is input into to a filtration routine 1336. Filtration is desirable because frequently, the waveform output by the ADC 1304 carries with it an undesirable amount of noise. Filtration routine 1336 can comprise any combination of instruction steps known in the art to result in an output signal whose magnitude is ascertainable.

Again referring to FIG. 13, the value that is output from the filtration routine 1336, referred to herein as a "point value" (1338), is stored in a memory resource at a point 1340 in time along process flow arrow 1342 arising prior to a time at which the point value 1338 enters the charge pump 1318. Once such storage occurs, the point value 1338 becomes the new input value for the charge pump 1318, to initiate a second iteration of the application of charge to the equivalent RC circuit 1306 at the test point 600. The charge pump 1318 produces a new pulse train, a length of high pulses in the new pulse train being proportional to the point value 1338, resulting in a subsequent magnitude of electrical charge applied at the test point 600, the subsequent magnitude corresponding to the point value 1338 and, tracing the aforementioned steps backward, also thereby corresponding to the ADC value output by the ADC. Over a predetermined number of iterations, a sequence of reading an ADC value and applying a subsequent magnitude of electrical charge to the test point 600 is repeated. In some implementations, sixty (60) iterations can be done to comprise a single measurement session, and to determine a point value average over at least a portion of the 60 iterations, wherein the point value average provides an indication of conductance of the combination of the potting compound 900 and the insulator 1100, from which relative moisture content in the potting compound can be ascertained.

Regarding the exemplary sixty (60) iterations, it has been found that such a number provides a stable way to ascertain conductance from operation of the system 1300. This allows time for a measured potting compound/insulator combination in a node 200 to "settle" to a final test point voltage in 60 iterations, whereas that voltage can still be "decaying" exponentially after a smaller number of iterations, such as 20 iterations. This is because exponential decay is the response of an RC circuit to voltage stimulus/discharge. Trying to ascertain a final point score from a measurement session with such a smaller number of iterations, while that exponential decay was still occurring, produced instability in the readings. In some implementations, the portion of the 60 iterations from which a point value average is determined can be the last twenty (20) iterations, as will be discussed in greater detail herein with regard to FIG. 18. The use of successive, newly-determined point values 1338 as successive inputs for the charge pump 1318 demonstrates the closed-loop characteristic of system 1300. This closed-loop characteristic is what allows one to observe changes in the charge held by the equivalent RC circuit 1306 over time, and it is that change which provides the basis for determining the point value average to determine conductance.

Figure 15:
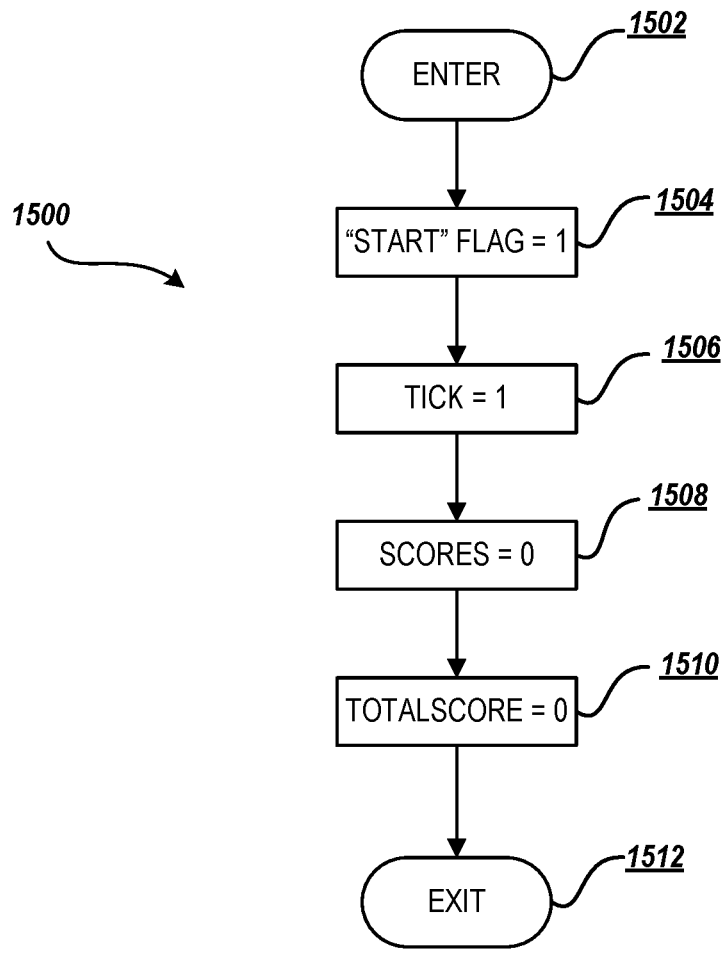
FIG. 15 is a flow chart diagram illustrating operation of a start routine in a potting moisture detection system according to aspects of the present disclosure.
Figure 16:
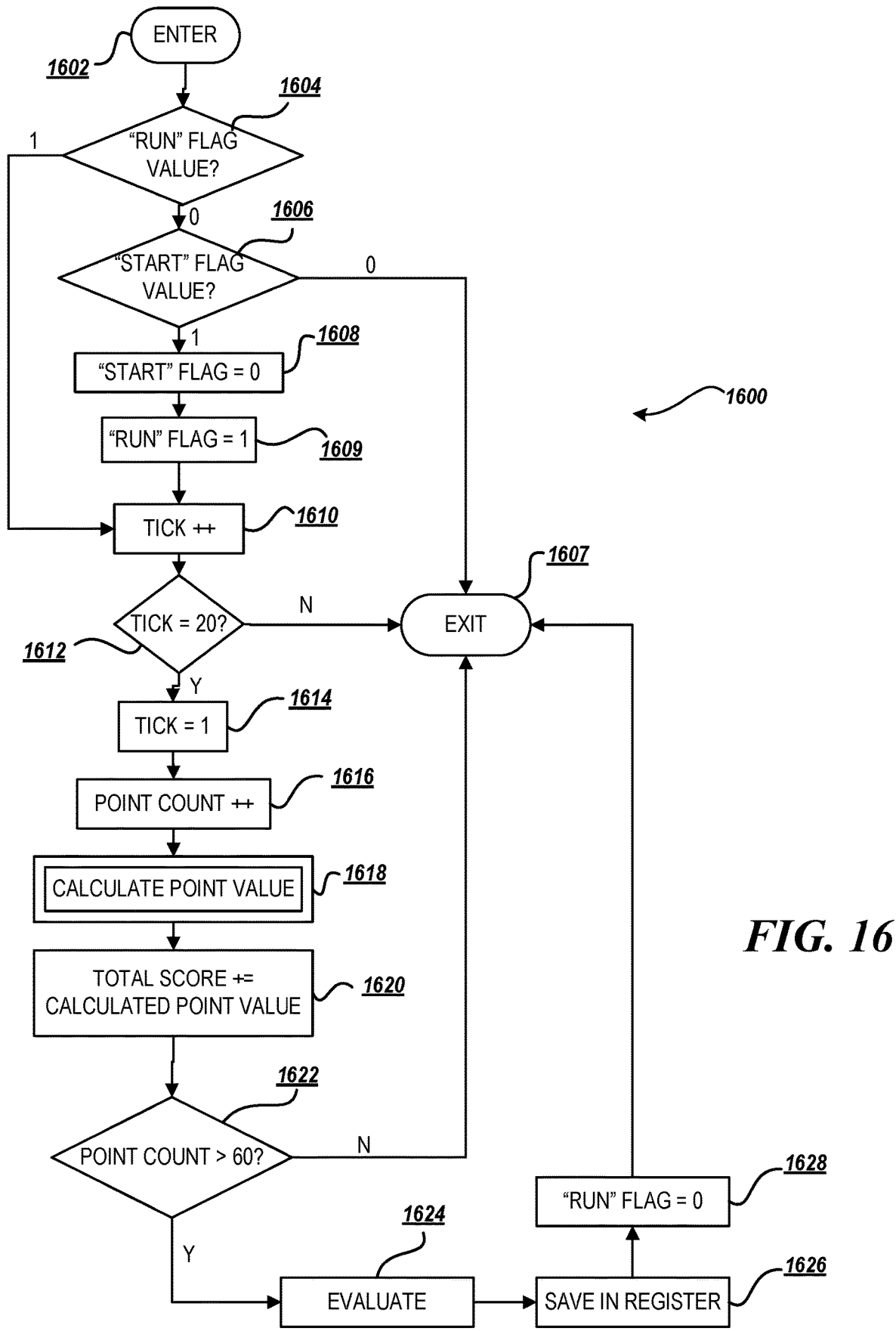
FIG. 16 is a flow chart diagram illustrating operation of a timing routine in a potting moisture detection system according to aspects of the present disclosure.

FIG. 15 is a flow chart diagram illustrating operation of a start routine 1500 in the potting moisture detection system 1300 of FIG. 13. Routine 1500 is called when a measurement test is started. In some implementations, routine 1500 can be started remotely through a command sent wirelessly by the host 102 to a node 200, such communications sent in the manner described above with regard to FIG. 1. In the example of FIG. 15, "start" block 1502 represents the sending of radio message the node 200, the message containing a command for the processor 220 to change a setting of a "start" flag within a register of its internal memory 221 (FIG. 2), a flag that can be set to either 1 or 0. As with all flags to be herein described, the "start" flag is a memory variable in the internal memory 221 that can be added and defined by a programmer when the program is compiled and loaded into the processor 220. The "start" flag is normally set to zero. In the start routine 1500, at block 1504, that flag is set to 1. When the "start" flag is set to 1, the "tick" value is also set to 1 at block 1506. A single "tick" represents one increment of time over which the timing routine 1600 of FIG. 16 executes. In the example discussed herein, one "tick" represents 0.75 seconds, the length of time it takes for timing routine 1600 to execute. Subsequent changes to the "tick" value are discussed herein with regard to blocks 1610, 1612, and 1614 of FIG. 16. At block 1508, the "SCORES" value, which represents the sum of all determined point values 1338 (FIG. 13), is set to zero when the "start" flag is set to 1. Finally, the "TOTALSCORE" value, which represents an average value as discussed in further detail below with regard to FIG. 16, is also set to zero at block 1510. The start routine 1500 then exits at block 1512, and the steps described below with regard to FIG. 16 commence.

FIG. 16 is a flow chart diagram illustrating operation of a timing routine 1600 in the potting moisture detection system 1300 of FIG. 13. Timing routine 1600 begins at block 1602 and advances to decision block 1604, wherein a value of a "RUN" flag is determined. Like the "start" flag discussed above, the "RUN" flag can have a value of either 0 or 1. A "1" value for this flag means that a measurement session (comprising 60 iterations/data points in the example discussed herein) is in progress, during which time other activities in the node 200 that normally run (such as radio and automatic activity starting) are shut down. A "0" value for the ""RUN" flag means that a measurement session is not in progress. If the "RUN" flag is set to 1, timing routine 1600 skips to block 1610, where the "tick" value is incremented by 1. If, however, the "RUN" flag is set to zero, then timing routine 1600 advances to decision block 1606. At decision block 1606, the value of the "start" flag setting is checked. If the "start" flag is 0, the timing routine 1600 exits at block 1607. Otherwise, the timing routine 1600 advances to block 1608, where the "start" flag is reset, from 1 to 0. This is necessary in order to prevent the start flag from re-triggering the start routine 1500 of FIG. 15, in which event the timing routine 1600 would be brought to an undesirable halt. Next, at block 1609, the "RUN" flag is set to 1, and the "tick" value is incremented by 1 at block 1610.

At decision block 1612 of FIG. 16, a decision is made as to whether the "tick" value has exceeded a count of 20. In the implementation illustrated, the "GO" flag is set to 1, prompting the ADC 1304 to output an ADC value in the manner discussed above, every 0.75 seconds. For there to be a chosen data point period of 15 seconds between point value determinations (data points), and with a "tick" lasting 0.75 seconds, there must be 20 "ticks" between data points. If, at decision block 1612, it has been determined that 20 "ticks" have not yet been reached, then the timing routine 1600 exits at block 1607. (Every 0.75 s, the routine 1600 wakes up, executes, and then completes, so the routine 1600 will repeat, beginning at the "enter" block 1602, if the 20 "ticks" have not yet been reached.) If, instead, the tick count exceeds 20, then that means timing routine 1600 has finished collecting readings for a particular data point, and timing routine 1600 proceeds to block 1614, where the "tick" value is reset to zero. Also, at block 1616, with collection of readings for that data point now concluded, the timing routine 1600 increments by 1 the POINT COUNT value. Next, at block 1618, the point value for that data point is calculated, in the manner to be described with regard to FIG. 17. Timing routine 1600 then proceeds to block 1620, which calculates the TOTALSCORE value by adding the value determined at block 1618 to a sum of all point values determined for any prior data points in the measurement session, then divides that sum by the new POINT COUNT value resulting from the incrementation at block 1616.

At decision block 1622 of FIG. 16, it is determined whether the POINT COUNT now exceeds a count of 60, in implementations where there are to be 60 iterations (data points) of test point voltage readings. If POINT COUNT has not yet exceeded 60, the timing routine 1600 exits at block 1607. If, however, the POINT COUNT now exceeds 60, then the timing routine 1600 advances to block 1624 for an evaluation of results, the manner of conducting such an evaluation to be discussed in detail with regard to FIG. 18. Next, at block 1626, the evaluation can be stored in a memory resource, including within a register of a CPU in the processor 220. Finally, with the measurement session now concluded, the "RUN" flag is reset to zero at block 1628, and the timing routine 1600 exits at block 1607.

Figure 17:
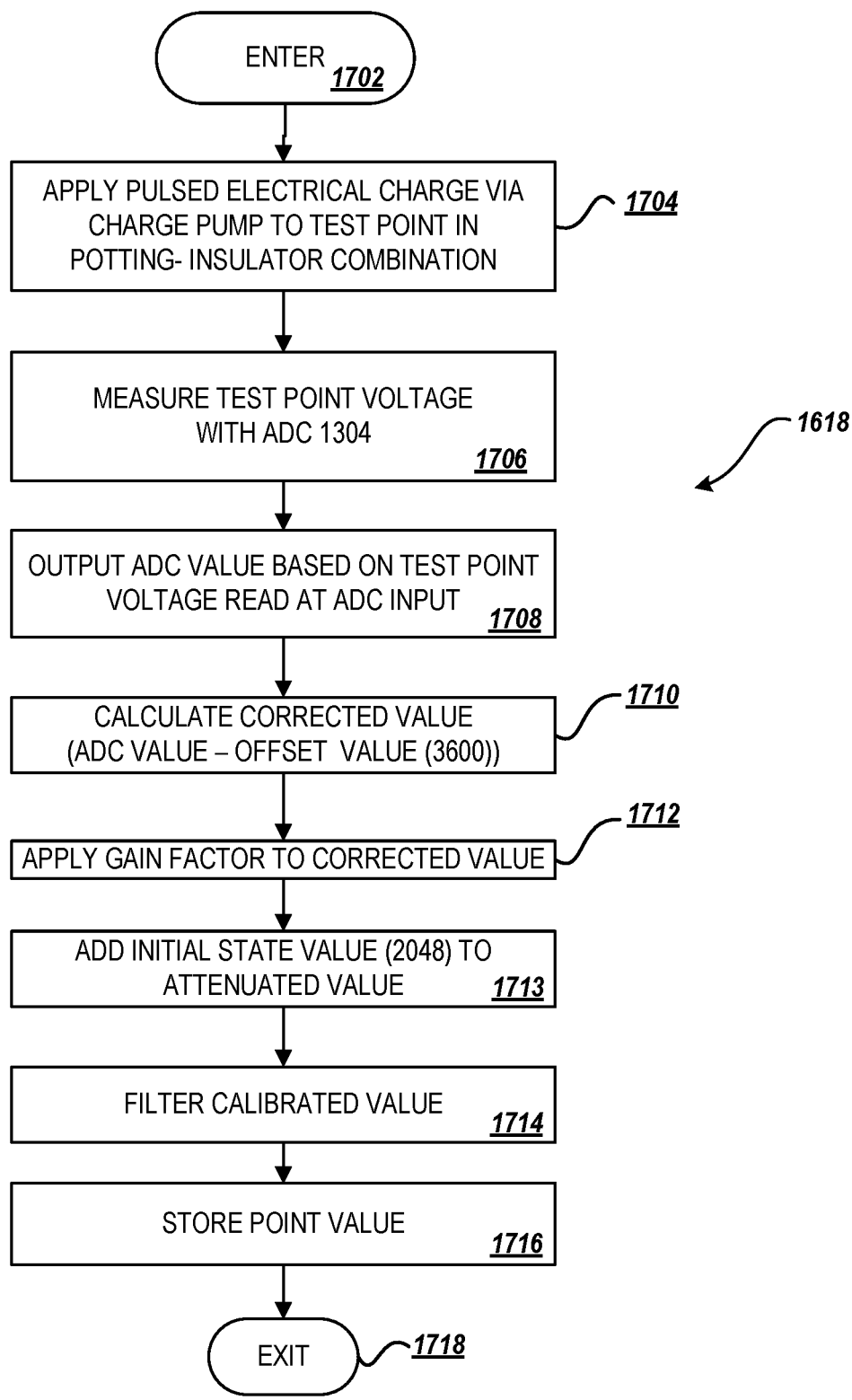
FIG. 17 is a flow chart diagram illustrating an algorithm for the "calculate point value" step shown in the flow chart diagram of FIG. 16.

FIG. 17 is a flow chart diagram illustrating an algorithm 1618 for the "calculate point value" step shown in FIG. 16 at 1618. Algorithm 1618 can be regarded as a summary of the steps in the operation of the potting moisture detection system 1300 discussed above with regard to FIG. 13. Algorithm 1618 begins at the entry block 1702, which occurs just after the POINT COUNT value has been incremented at block 1616 of FIG. 16, and advances to block 1704, where the charge pump 1318 (FIG. 13) applies the pulsed electrical charge to the equivalent RC circuit 1306 in the manner described above with regard to FIGS. 13, 14A, and 14B. After a predetermined delay period which, as stated above, can range from 100 µs to 10 ms, algorithm 1618 advances to block 1706, in which the ADC 1304 measures the test point voltage of the equivalent RC circuit 1306. Next, at block 1708, the ADC 1304 outputs an ADC value in the manner discussed above with regard to FIG. 13. Next, as also described with regard to FIG. 13: (a) algorithm 1618 advances to block 1710, where an offset value 1328 is subtracted from the ADC value to result in a corrected value; (b) at block 1712, the gain factor is applied to the corrected value to produce an attenuated value; (c) at block 1713, an initial state value 1334 is added to the corrected value to produce a calibrated value; (d) at block 1714, that calibrated value is then filtered with any known conventional filtering routines to produce a point value; (e) algorithm 1618 then advances to block 1716, in which the point value is stored in a memory resource; and (f) algorithm 1618 then exits at block 1718. In the example presented above, a 60-point measurement session would take 15 minutes, since there is a data point period of 15 seconds between each data point. In some implementations, for optimal operation of system 1300, a user should allow at least 12 hours between measurement sessions to allow charge to dissipate from the equivalent capacitor 1308 (FIG. 13).

Figure 18:
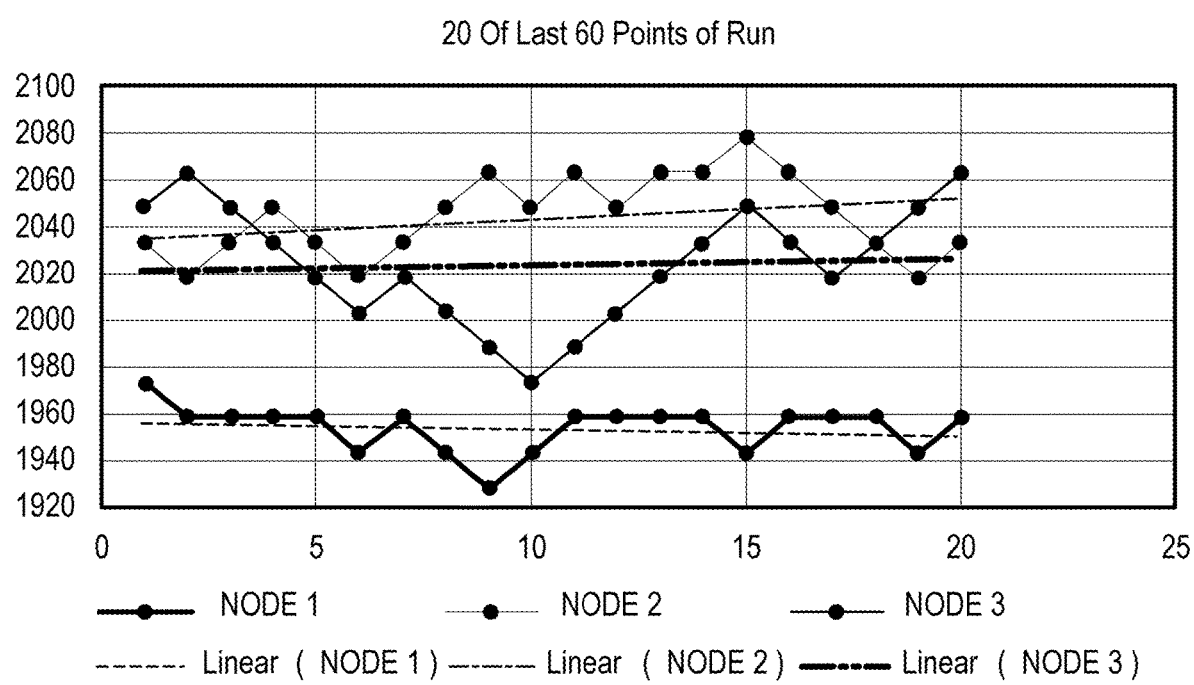
FIG. 18 is a diagram illustrating exemplary plots of the final twenty (20) point value determinations in three measurement sessions for three corresponding nodes, according to aspects of the present disclosure.

FIG. 18 is a diagram illustrating exemplary plots of the final twenty (20) point value determinations in three measurement sessions for three corresponding nodes, according to aspects of the present disclosure. The vertical axis represents an example range of ADC-based point values (here, ranging from 1920 to 2100). The horizontal axis represents numbers counting up the number of the point calculated. In a 60-point measurement session, the first value on the horizontal axis could be 40 instead of zero, and the final value could be 60 instead of 20, but the depicted horizontal range from 0 to 20 is shown for ease of illustration. The graph of FIG. 18 only shows the last 20 points of each of the three measurements sessions, because it has been found that, beginning around the $41^{st}$ point of a 60-point measuring session, the exponential decay in the potting compound/insulator combination within the node 200 concludes, such that by that point, that combination now only produces a straight-line voltage response to the application of pulsed electrical charge. The node 200 can therefore be programmed to, at the conclusion of each 60-point measurement session, wirelessly communicate to a network element (such as the host 102 of FIG. 1) the point values of only the last 20 data points in the measurement session.

Still referring to FIG. 18, the "Linear" dashed lines extending across the plots of Node 1, Node 2, and Node 3 represent respective "least square curve fits" of each of these plots, each dashed line approximating the mathematical average point value of the corresponding 20 data points shown. Programming can precisely and automatically determine the least square curve fit for each 20-point plot. A visual inspection of these linear plots indicates that Node 1 has an average point value of around 1955, that Node 2 has an average point value of around 2045, and that Node 3 has an average point value of around 2022. Software stored in a memory resource can pinpoint each average with greater accuracy, and determine the least square curve fit for each 20-point plot. Such averages, linear plots, or raw data can be part of the data communicated by the node 200 to the host 102.

Next, as at least part of the "Evaluate" step 1624 in FIG. 16, a reported average point value is compared against known thresholds that can be established by using system 1300 (FIG. 13) to take measurements on nodes that are known to be damaged and known to be dry. For example, if a node known to be completely dry undergoes a measurement session by the system 1300, and that node registers an average point value of, say, 2050, that average point value could be used as a benchmark against which other nodes may be compared. (Note here, however, that some point values manage to exceed 2050 due to high waveform filtering slew rates that can move waveform counts as high as 13 units.) A node known to be damaged could, hypothetically, register an average point value of 1940. Thus, in such an instance, nodes presently residing in networks that register average point values closely approaching 1940 would be the subject of remedial actions as their scores would indicate a strong probability that the units are wet and, therefore, damaged. Between the two extremes (completely dry and damaged), other nodes known to be sufficiently-though-not-completely dry, and known to be not damaged but still unacceptably wet, can also be tested to establish intermediate thresholds indicative of whether a node falling between the two aforementioned extremes is still in satisfactory condition such that an owner would not need to take remedial action for it. An evaluation of a given point value average could be expressed as a percentage indicating how far the average point value falls below the completely-dry point benchmark. This can be done by taking a ratio of a numerator comprising the difference between the completely-dry and the reported point value scores, and a denominator quantifying a "span" for the final 20 data points. For instance, using the aforementioned extremes, the span of these data points could be 2050−1940=110. Then, with reference to the visually-determined average point values, Node 1 has a ratio of (2050−1955)/110=86% of the span below the completely-dry benchmark (2050), which would clearly mean a damaged node. For comparison, Node 2 has a ratio of (2050−2045)/110=only 4.5% of the span below the completely-dry benchmark, indicative of a satisfactory node. Finally, Node 3 has a ratio of (2055−2022)/110=30% of the span below the completely-dry benchmark. Whether that ratio indicates an acceptable node would have to be assessed against established intermediate thresholds. For example, if it is established that any ratio over 12% indicates that the moisture in the potting compound of the tested node is unacceptably high, then Node 3, like Node 1, would be targeted for remedial measures.

Although several aspects have been disclosed in the foregoing specification, it is understood by those skilled in the art that many modifications and other aspects will come to mind to which this disclosure pertains, having the benefit of the teaching presented in the foregoing description and associated drawings. It is thus understood that the disclosure is not limited to the specific aspects disclosed hereinabove, and that many modifications and other aspects are intended to be included within the scope of any claims that can recite the disclosed subject matter.

One should note that conditional language, such as, among others, "can," "could," "might," or "may," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily comprise logic for deciding, with or without user input or prompting, whether these features, elements and/or steps are included or are to be performed in any particular aspect.

It should be emphasized that the above-described aspects are merely possible examples of implementations, merely set forth for a clear understanding of the principles of the present disclosure. Any process descriptions or blocks in flow diagrams should be understood as representing modules, segments, or portions of code which comprise one or more executable instructions for implementing specific logical functions or steps in the process, and alternate implementations are included in which functions may not be included or executed at all, can be executed out of order from that shown or discussed, including substantially concurrently or in reverse order, depending on the functionality involved, as would be understood by those reasonably skilled in the art of the present disclosure. Many variations and modifications can be made to the above-described aspect(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A node, comprising:
   a circuit board assembly comprising a circuit board and a processor mounted to the circuit board, the processor comprising a pin and an analog-to-digital converter (ADC) in electrical communication with the pin, the circuit board defining a test point formed therein, the test point electrically communicating with the pin via a trace covered with an insulator; and
   a non-transitory memory resource, the non-transitory memory resource having computer-executable instructions stored thereon that, when executed by the processor, cause the processor to
      apply electrical charge to the test point after the circuit board assembly has been encased in a potting compound, and
      command the ADC to read a test point voltage at the test point, the test point voltage indicating voltage of an equivalent resistor-capacitor (RC) circuit comprising the insulator as an equivalent capacitor and the potting compound as an equivalent resistor;
   wherein the processor further comprises a switch configured to selectively assume a first position, a second position, and a third position, the first position bringing the equivalent RC circuit into electrical communication with a voltage source, the second position resulting in an open circuit between the voltage source and the equivalent RC circuit, and the third position bringing the equivalent RC circuit into electrical communication with an electrical ground; and
   wherein the computer-executable instructions, when executed by the processor, further cause the processor to
      selectively bring the switch into one of the first position, the second position, and the third position,
      implement a switching sequence between the first, second, and third positions to result in a pulse train, the pulse train having a length of high pulses, the length of high pulses being proportional to a first magnitude of electrical charge to be applied to the test point,
      read an ADC value at an output of the ADC, the ADC value expressed as a number corresponding to the test point voltage read by the ADC,
      apply a subsequent magnitude of electrical charge to the test point, the subsequent magnitude of electrical charge corresponding to the ADC value,
      repeat, for a predetermined number of iterations, a sequence of reading an ADC value and applying a subsequent magnitude of electrical charge to the test point, and
      determine a point value average over at least a portion of the predetermined number of iterations,
      wherein the point value average provides an indication of conductance of a combination of the potting compound and the insulator, from which relative moisture content in the potting compound can be ascertained.

2. The node of claim 1, wherein the computer-executable instructions, when executed by the processor, further cause the processor to command the ADC to read the test point voltage after lapse of a predetermined delay period.

3. The node of claim 2, wherein the predetermined delay period ranges from and including 100 μs (microseconds) to and including 10 ms (milliseconds).

4. The node of claim 1, wherein the portion of the predetermined number of iterations comprises a final twenty (20) iterations of the predetermined number of iterations.

5. The node of claim 4, wherein the predetermined number of iterations comprises sixty (60) iterations.

6. The node of claim 1, wherein the computer-executable instructions, when executed by the processor, further cause the processor to subtract an offset value from the ADC value, the offset value corresponding to an ambient voltage at the test point before application of electrical charge to the test point, subtraction of the offset value resulting in a corrected value.

7. The node of claim 6, wherein the computer-executable instructions, when executed by the processor, further cause the processor to multiply the corrected value by a gain factor to produce an attenuated value.

8. The node of claim 7, wherein the computer-executable instructions, when executed by the processor, further cause the processor to add an initial state value to the attenuated value to produce a calibrated value, the initial state value corresponding to the first magnitude of electrical charge.

9. The node of claim 8, wherein the computer-executable instructions, when executed by the processor, further cause the processor to
   subject the calibrated value to a filtration routine to produce a point value,
   store the point value in the non-transitory memory resource, and
   produce a new pulse train, a length of high pulses in the new pulse train being proportional to the point value.

10. The node of claim 9, further comprising potting compound encasing the circuit board.

11. A potting moisture detection system, comprising:
   a host, the host configured to communicate with a plurality of nodes and to receive point value data from at least one node in the plurality of nodes; and
   the node of claim 10, the node of claim 10 comprising at least one node in the plurality of nodes, the node of claim 10 further configured to send the point value data to the host responsive to receiving a command from the host to transmit the point value data.

12. A method, comprising the steps of:
   applying electrical charge to a test point in a circuit board assembly after the circuit board assembly has been encased in a potting compound, the circuit board assembly comprising a circuit board and a processor mounted to the circuit board, the processor comprising a pin and an analog-to-digital converter (ADC) in electrical communication with the pin, the circuit board defining the test point formed therein, the test point electrically communicating with the pin via a trace covered with an insulator;
   after lapse of a predetermined delay period, commanding the ADC to read a test point voltage at the test point, the test point voltage indicating voltage of an equivalent resistor-capacitor (RC) circuit comprising the insulator as an equivalent capacitor and the potting compound as an equivalent resistor;
   wherein the processor further comprises a switch configured to selectively assume a first position, a second position, and a third position, the first position bringing the equivalent RC circuit into electrical communication with a voltage source, the second position resulting in an open circuit between the voltage source and the equivalent RC circuit, and the third position bringing the equivalent RC circuit into electrical communication with an electrical ground;
   selectively bringing the switch into one of the first position, the second position, and the third position;
   implementing a switching sequence between the first, second, and third positions to result in a pulse train, the pulse train having a length of high pulses, the length of high pulses being proportional to a first magnitude of electrical charge to be applied to the test point;
   reading an ADC value at an output of the ADC, the ADC value expressed as a number corresponding to the test point voltage read by the ADC;
   applying a subsequent magnitude of electrical charge to the test point, the subsequent magnitude of electrical charge corresponding to the ADC value; and
   repeating, for a predetermined number of iterations, the steps of reading an ADC value and applying a subsequent magnitude of electrical charge to the test point; and
      determining a point value average over at least a portion of the predetermined number of iterations;
   wherein the point value average provides an indication of conductance of a combination of the potting compound and the insulator, from which relative moisture content in the potting compound can be ascertained.

13. The method of claim 12, wherein the predetermined number of iterations comprises sixty (60) iterations, and wherein the portion of the predetermined number comprises a final twenty (20) iterations of the sixty iterations.

14. The method of claim 12, further comprising the steps of:
   subtracting an offset value from the ADC value, the offset value corresponding to an ambient voltage at the test point before application of electrical charge to the test point, subtraction of the offset value resulting in a corrected value;
   multiplying the corrected value by a gain factor to produce an attenuated value; and
   adding an initial state value to the attenuated value to produce a calibrated value, the initial state value corresponding to the first magnitude of electrical charge.

15. The method of claim 14, further comprising the steps of:
   filtering the calibrated value to produce a point value;
   storing the point value in a non-transitory memory resource; and
   producing a new pulse train, a length of high pulses in the new pulse train being proportional to the point value.

* * * * *